United States Patent
Partanen et al.

(10) Patent No.: US 11,116,405 B2
(45) Date of Patent: Sep. 14, 2021

(54) HIGH-INTENSITY FOCUSED ULTRASOUND FOR HEATING A TARGET ZONE LARGER THAN THE ELECTRONIC FOCUSING ZONE

(71) Applicants: Profound Medical Inc., Mississauga (CA); THE GOVERNMENT OF THE UNITED STATES, AS REPRESENTED BY THE SECRETARY OF HEALTH & HUMAN SERVICES, NATIONAL INSTITUTES OF HEALTH, OFFICE OF TECHNOLOGY TRANSFER, Bethesda, MD (US)

(72) Inventors: Ari Ilkka Mikael Partanen, Bethesda, MD (US); Matthew Robert Dreher, Rockville, MD (US); Pavel Sergeyevich Yarmolenko, Germantown, MD (US); Bradford Johns Wood, Bethesda, MD (US); Elma Natalia Carvajal Gallardo, Enschede (NL)

( * ) Notice: Subject to any disclaimer, the term of this patent is extended or adjusted under 35 U.S.C. 154(b) by 1554 days.

(21) Appl. No.: 14/390,181

(22) PCT Filed: Apr. 9, 2013

(86) PCT No.: PCT/IB2013/052806
§ 371 (c)(1),
(2) Date: Oct. 2, 2014

(87) PCT Pub. No.: WO2013/153506
PCT Pub. Date: Oct. 17, 2013

(65) Prior Publication Data
US 2015/0080705 A1  Mar. 19, 2015

Related U.S. Application Data

(60) Provisional application No. 61/623,355, filed on Apr. 12, 2012.

(51) Int. Cl.
A61B 5/00 (2006.01)
A61N 7/02 (2006.01)
(Continued)

(52) U.S. Cl.
CPC ............ *A61B 5/0036* (2018.08); *A61B 5/015* (2013.01); *A61B 5/055* (2013.01); *A61B 5/7253* (2013.01);
(Continued)

(58) Field of Classification Search
CPC combination set(s) only.
See application file for complete search history.

(56) References Cited

U.S. PATENT DOCUMENTS 5,984,881 A    11/1999  Ishibashi et al.
6,618,620 B1 *  9/2003  Freundlich ............... A61N 7/02
                                                        600/437
(Continued)

FOREIGN PATENT DOCUMENTS

JP    H0884740 A    9/1994
JP    H11313831 A   11/1999
(Continued)

OTHER PUBLICATIONS

M. O. Kohler, C. Mougenot, B. Quesson et al., "Volumetric HIFU ablation under 3D guidance of rapid MRI thermometry," Med Phys, vol. 36, No. 8, pp. 3521-3535, Aug. 2009.
(Continued)

*Primary Examiner* — Serkan Akar
*Assistant Examiner* — Helene Bor
(74) *Attorney, Agent, or Firm* — Intrinsic Law Corp.

(57) ABSTRACT

The invention provides for a medical instrument (200) comprising a magnetic resonance imaging system (202) and a high-intensity focused ultrasound system (204) with an electronically controllable and a mechanically controllable
(Continued)

focus. Execution of instructions by a processor (244) controlling the instrument cause the processor to: receive (100) a target zone (240, 264) descriptive of a zone within the subject; divide (102) the target zone into multiple sub-zones (416, 418, 420, 422, 424, 426, 428, 430, 432, 434); determine (104) a sequence (272) for moving the transducer position to each of the multiple sub-zones; determine (106) a selected sub-zone selected from the multiple sub-zones using the sequence; repeatedly control (108) the mechanical positioning system to move the transducer to the transducer position of the selected sub-zone; repeatedly acquire (110) the magnetic resonance thermometry data; repeatedly determine (112) a temperature property map (274); repeatedly heat (114) the regions independently to the target temperature by controlling the electronically controlled focus with a temperature feedback algorithm (286); and repeatedly change (116) the selected sub-zone using the sequence.

17 Claims, 9 Drawing Sheets

(51) Int. Cl.
    *A61B 34/10*     (2016.01)
    *A61B 5/01*     (2006.01)
    *A61B 5/055*     (2006.01)
    *A61N 7/00*     (2006.01)
    *A61B 18/00*     (2006.01)
    *A61B 17/00*     (2006.01)
    *A61B 90/00*     (2016.01)

(52) U.S. Cl.
    CPC ............ *A61B 5/7264* (2013.01); *A61B 34/10* (2016.02); *A61N 7/02* (2013.01); *A61B 2017/00084* (2013.01); *A61B 2018/00791* (2013.01); *A61B 2090/374* (2016.02); *A61N 2007/0091* (2013.01); *A61N 2007/0095* (2013.01)

(56) References Cited

U.S. PATENT DOCUMENTS

| | | | |
|---|---|---|---|
| 7,699,780 B2 | 4/2010 | Vitek et al. | |
| 8,038,631 B1 | 10/2011 | Sanghvi et al. | |
| 8,845,559 B2 | 9/2014 | Darlington et al. | |
| 9,095,695 B2 | 8/2015 | Fedewa et al. | |
| 9,399,148 B2 | 7/2016 | Annaud et al. | |
| 2005/0240127 A1* | 10/2005 | Seip | A61N 7/02 601/2 |
| 2007/0239062 A1* | 10/2007 | Chopra | A61B 5/01 600/549 |
| 2009/0198131 A1 | 8/2009 | Fedewa et al. | |
| 2010/0210976 A1 | 8/2010 | Darlington et al. | |
| 2010/0280356 A1* | 11/2010 | Kohler | A61N 7/02 600/411 |
| 2011/0087103 A1* | 4/2011 | Gross | A61N 7/02 600/444 |
| 2011/0251607 A1* | 10/2011 | Kruecker | A61B 18/1206 606/34 |
| 2011/0270075 A1 | 11/2011 | Vitek et al. | |
| 2011/0270136 A1* | 11/2011 | Vitek | A61N 7/02 601/2 |
| 2012/0071746 A1* | 3/2012 | Vortman | G01R 33/4804 600/411 |
| 2013/0345547 A1 | 12/2013 | Vahala | |
| 2014/0005523 A1 | 1/2014 | Kohler et al. | |
| 2014/0277035 A1* | 9/2014 | Strait | A61N 7/02 606/169 |
| 2015/0112235 A1* | 4/2015 | Brasset | A61N 7/02 601/3 |

FOREIGN PATENT DOCUMENTS

| | | |
|---|---|---|
| JP | 2091231762 A | 8/2001 |
| JP | 2004105502 A | 4/2004 |
| JP | 2013022391 A | 2/2013 |

OTHER PUBLICATIONS

R. Staruch, R. Chopra, and K. Hynynen, "Localised drug release using MRI-controlled focused ultrasound hyperthermia," Int J Hyperthermia, vol. 27, No. 2, pp. 156-171, 2011.

P. M. Harari, K. H. Hynynen, R. B. Roemer et al., "Development of scanned focussed ultrasound hyperthermia: clinical response evaluation," Int J Radiat Oncol Biol Phys, vol. 21, No. 3, pp. 831-840, Aug. 1991.

J. K. Enholm, M. O. Kohler, B. Quesson et al., "Improved volumetric MR-HIFU ablation by robust binary feedback control," IEEE Trans Biomed Eng, vol. 57, No. 1, pp. 103-113, Jan. 2010.

M. de Smet, Edwin Heijman, Sander Langereis et al., "Magnetic resonance imaging of high intensity focused ultrasound mediated drug delivery from temperature-sensitive liposomes: An in vivo proof-of-concept study", Journal of Controlled Release 150 (2011) pp. 102-110.

A.H. Negussie, P.S. Yarmolenko, A. Partanen et al., "Formulation and characterisation of magnetic resonance imageable thermally sensitive liposomes for use with magnetic resonance-guided high intensity focused ultrasound", Int. J. Hyperthermia, Mar. 2011; 27(2), pp. 140-155.

A. Ranjan, G.C. Jacobs, D.L. Woods et al., "Image-guided drug delivery with magnetic resonance guided high intensity focused ultrasound and temperature sensitive liposomes in rabbit Vx2 tumor model", Journal of Controlled Release (2012), doi:10.1016.

* cited by examiner

HIGH-INTENSITY FOCUSED ULTRASOUND FOR HEATING A TARGET ZONE LARGER THAN THE ELECTRONIC FOCUSING ZONE

CROSS-REFERENCE TO PRIOR APPLICATIONS

This application is the U.S. National Phase application under 35 U.S.C. § 371 of International Application Serial No. PCT/IB2013/052806, filed on Apr. 9, 2013, which claims the benefit of U.S. Application Ser. No. 61/623,355, filed on Apr. 12, 2012. These applications are hereby incorporated by reference herein.

This invention was made with Government support under Cooperative Research and Development Agreement No. 01864, dated Dec. 16, 2004, with the United States Public Health Service. The government has certain rights in this invention.

TECHNICAL FIELD

The invention relates to high-intensity focused ultrasound, in particular to magnetic resonance guided high-intensity focused ultrasound.

BACKGROUND OF THE INVENTION

The invention pertains to a MR image guided high-intensity focused ultrasound (HIFU) therapy system. The HIFU module comprises an ultrasound transducer (array) with transducer elements that emit the HIFU beams. The focus can be steered over a local range by electronically control the phase of each of the element (electronic steering).

SUMMARY OF THE INVENTION

The invention provides for a medical instrument and a computer program product in the independent claims. Embodiments are given in the dependent claims.

According to one embodiment of the invention, a large target region into which ultrasound (US) energy is to be deposited is segmented into several local regions. Within individual local regions, US energy is deposited by scanning the focus within the local region by way of electronic steering. Further the transducer (array) is repositioned for each of the local regions.

The invention may enable the application of HIFU treatment (by way of the deposition of ultrasonic energy) in a large target region of arbitrary shape. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus.

Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic and/or functional data contained within the magnetic resonance imaging data. This visualization can be performed using a computer.

Medical image data as used herein encompasses data which is descriptive of anatomical structures of a subject. A magnetic resonance image is a type of medical image data.

Magnetic Resonance (MR) thermometry data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical instrument comprises a magnetic resonance imaging system for acquiring magnetic resonance data from a subject within an imaging zone. The medical instrument further comprises a high-intensity focused ultrasound system comprising an ultrasound transducer with an electronically controllable focus. The electronically controllable focus may be implemented by using an ultrasound transducer which has multiple transducer elements. The phase and/or amplitude of ultrasound may be controlled such that the additive and destructive effects of multiple ultrasound signals cause the focus to shift position. The high-intensity focused ultrasound system further comprises a mechanical positioning system for positioning the ultrasound transducer. The mechanical positioning system may physically move the ultrasound transducer to different locations.

Typically, the mechanical positioning system is used for gross control of the focus and the electronic control is used for fine control of the focus. The electronically controlled focus is operable to adjust the focus within a focusing zone. The focusing zone as used herein encompasses a region above which the intensity of the focus is above a predetermined intensity. As the focus is moved electronically the intensity of the ultrasound may decrease. The operator or manufacturer of a high-intensity focused ultrasound system may choose the intensity limit which defines a focusing zone. The location of the focusing zone is dependent upon the position of the ultrasound transducer. As the ultrasound transducer is physically moved by the mechanical positioning system the location of the focusing zone changes with the change in location of the ultrasound transducer.

The medical instrument further comprises a memory for storing machine-executable instructions. The medical instrument further comprises a processor for controlling the medical instrument. Execution of the instructions causes the processor to receive a target zone descriptive of a volume within the subject. The target zone may also be referred to as a target volume. The target zone may for instance be defined on a graphical user interface or it may be received as part of a treatment plan. In any case the target zone may describe a volume within the subject and may also contain such things as anatomical references which allow the target zone to be registered to the location of the subject. A volume as used herein may represent a two-dimensional or three-dimensionally specified target zone. Typically in planning and imaging two-dimensional images are used. However, these two dimensional images necessarily represent volumes. In magnetic resonance imaging the data is typically displayed as "slices" or two dimensional regions of a subject. Each voxel in the two-dimensional image represents a contribution mostly from a small volume. The MRI images are reconstructed using a Fourier transform, so regions outside of a particular volume may also contribute to the image in a particular voxel. Likewise when a region is sonicated planning may be done using two-dimensional images. When a target is actually sonicated, the ultrasound heats a small volume of the subject.

The target zone is larger than the focusing zone. This may imply that in order to sonicate or heat the entire target zone the mechanical positioning system must be moved to more than one location. Execution of the machine-executable instructions further cause the processor to divide the target zone into multiple sub-zones. A sub-zone may also be referred to as a subzone, subvolume, or sub-volume. Each of the multiple sub-zones has a transducer position. When the transducer is at the transducer position the focusing zone comprises the sub-zone.

Execution of the instructions further cause the processor to determine a sequence for moving the transducer position to each of the multiple sub-zones. A sequence as used herein may broadly define a list or sequence of positions which the ultrasound transducer is moved to such that each of the multiple sub-zones is selected. In some instances the sequence may be determined on the fly such as through the use of a decision tree. In other embodiments the sequence is predefined but may be modified later by a suitable algorithm. In some instances the sequence only specifies a first sub-zone to be heated and then a selection algorithm such as a decision tree is used to select each of the subsequent sub-zones which are heated.

Execution of the instructions further cause the processor to determine a selected sub-zone selected from the multiple sub-zones using the sequence. Each of the sub-zones is divided into regions. Execution of the instructions further cause the processor to maintain the target zone at a target temperature for a predetermined time duration by repeatedly controlling the mechanical positioning system to move the transducer to the transducer position of the selected sub-zone. The target temperature may interpreted as being a temperature range. The predetermined time duration may also be adjustable or changed on the fly during operation.

The selected sub-zone has a position for the mechanical transducer associated with it and the mechanical positioning system moves the ultrasound transducer there such that the focusing zone encompasses the selected sub-zones so that it may be heated. Execution of the instructions further causes the processor to maintain the target zone at the target temperature for the predetermined time by repeatedly acquiring the magnetic resonance thermometry data.

The magnetic resonance thermometry data is descriptive of the temperature of voxels in the sub-zone. It is important to note that the data is only descriptive of the temperature of voxels in the sub-zone. There may be certain properties such as the T1 value, T2 value or elasticity of the tissue in a particular voxel which may be indicative of the temperature. Control algorithms may be used which use this temperature dependent magnetic resonance data instead of using the temperature data directly. However, the magnetic resonance data may also be processed so that the temperature is displayed in each of the voxels and this is used to directly control the process.

Execution of the instructions further causes the processor to maintain the target zone at the target temperature for the predetermined time duration by repeatedly determining a temperature property map descriptive of the temperature in each of the voxels using at least the magnetic resonance thermometry data. The temperature property map may be the temperature, it may be some average or other value calculated statistically from temperature values, or it may be a property which is temperature-dependent such as the T1 value, the spin phase, the T2 or other properties. Execution of the instructions further causes the processor to maintain the target zone at the target temperature for the predetermined time duration by repeatedly heating the regions independently to the target temperature by controlling each of the electronically controlled focus with a temperature feedback algorithm that uses the temperature property map.

In an embodiment each of the regions corresponds to a voxel. In other embodiments each of the regions corresponds to part of a voxel or multiple voxels.

The control algorithm is region-based. Each of the regions is evaluated independently and is subjected to a control algorithm which controls the electronic control focus to heat each region appropriately. Execution of the instructions further cause the processor to maintain the target zone at the target temperature for a predetermined time duration by repeatedly changing the selected sub-zone using the sequence. This may include simply following a list of sub-zones to heat or it may involve the use of a more complicated algorithm which modifies the sequence on the fly or even may select the next sub-zone on the fly.

This embodiment may be beneficial because it provides a means for effectively heating large areas of the subject to a particular temperature. This may be used for tissue ablation but may be particularly beneficial when maintaining the temperature of the target zone below a value which induces tissue necrosis.

In another embodiment execution of the instructions further cause the processor to determine a temperature property for each of the multiple sub-zones using the magnetic resonance thermometry data. The temperature property may for instance be a statistical property of the temperature property map for each of the multiple sub-zones. By way of example the minimum temperature, the maximum temperature, or the average temperature may be selected as the temperature property and used. In other cases, other values such as the T1, the T2 or other parameters which show a temperature dependence may also be used. Execution of the instructions further cause the processor to select a next sub-zone using the temperature property for each of the multiple sub-zones.

For instance an algorithm or a decision tree algorithm may be used to select the next sub-zone. For instance if the average temperature were selected the sub-zone with the lowest average temperature might be selected in some embodiments. Execution of the instructions further causes the processor to modify the sequence such that the next sub-zone is sequentially next in the sequence.

This embodiment may be beneficial because it enables on the fly navigation of the next sub-zone to be heated. The steps in this embodiment may be performed repeatedly to maintain the temperature of the entire target zone at a predetermined time.

In another embodiment execution of the instructions further cause the processor to control the mechanical positioning system to move the ultrasound transducer to the transducer position for each of the multiple sub-zones before heating the target zone to the target temperature. This embodiment may be beneficial because various properties of the magnetic field may change when the mechanical positioning system is moved to different locations. Moving the mechanical positioning to each of the positions before beginning the heating process may enable measurement of properties which affect the MR measurements and also may enable the ability to perform test ultrasound exposures or test shots before commencement of the heating process.

In another embodiment execution of the instructions further cause the processor to acquire calibration magnetic resonance thermometry data while at the transducer position for each of the multiple sub-zones before heating the target zone to the target temperature. The temperature property map is determined using at least the calibration magnetic resonance data. In order to perform accurate temperature measurements it may be necessary using some techniques such as the spin phase technique to perform a baseline calibration measurement.

In another embodiment execution of the instructions further cause the processor to perform a test ultrasonic exposure using the high-intensity focused ultrasound system while at the transducer position for at least two or each of the multiple sub-zones before heating the target zone to the target temperature. Execution of the instructions further cause the processor to determine an electronic focus correction for each of the multiple sub-zones and/or adjust the location of the focus zone for each of the multiple sub-zones and/or calculate a temperature rise rate for each of the multiple sub-zones. This embodiment may be beneficial because it may provide for different means of correcting the use of the medical instrument before commencing the heating process.

In another embodiment execution of the instructions further cause the processor to repeatedly calculate the perfusion coefficients and/or diffusion coefficients for each of the voxels using magnetic resonance data. Additional magnetic resonance data may be acquired during the acquisition of the magnetic resonance thermometry data or also may be derived from some of the same pulse sequences. This data may be used to correct the perfusion and/or diffusion coefficients in each of the voxels.

In another embodiment the temperature feedback control algorithm has temperature control algorithm parameters. The temperature control algorithm parameter is a constant value which is used in the mathematical formula which is used by the temperature feedback control algorithm. Changing the temperature control algorithm parameters changes the behavior of the temperature feedback control algorithm. Execution of the instructions further cause the processor to repeatedly recalculate the temperature control algorithm parameters using the perfusion coefficients and/or diffusion coefficients. For instance when the high-intensity focused ultrasound system begins to heat the target zone there may be a set of assumed temperature control algorithm parameters. As the system is functioning in heating the target zone the perfusion coefficients and/or diffusion coefficients may be calculated during the process and this may be used to recalculate the temperature control algorithm parameters which thereby improves the functioning of the temperature feedback control algorithm.

In another embodiment the temperature feedback control algorithm is any one of the following: a binary temperature control algorithm, a proportional temperature control algorithm, a proportional-integral temperature control algorithm, and a proportional-integral-derivative temperature control algorithm.

In another embodiment the target zone is divided into multiple sub-zones using medial axial transformation.

In another embodiment the medical instrument comprises a fluid cooling system that circulates a fluid for cooling the subject. The fluid cooling system is operable for maintaining the fluid at an operating temperature. This for instance may be a tube or cooling pad which is placed on the surface of the subject and is used to remove excess heat. A chiller or other cooling system may maintain the fluid at a constant temperature. Execution of the instructions further causes the processor to repeatedly acquire magnetic resonance data descriptive of the spin phase of the fluid to determine a change in the spin phase. For instance if the spin phase method of measuring the temperature is used it is advantageous to repeatedly make phase measurements to calibrate the measurement. For instance there may be changes in the magnetic field which causes the spin phase to drift during the use of the medical instrument.

If the fluid in the fluid cooling system is maintained at a constant temperature such that a steady state is reached then the fluid within the fluid cooling system may be used as a reference. The spin phase may drift due to changes in the magnetic field but the temperature will be the same and this may be used as a reference measurement. Execution of the instructions further causes the processor to correct the temperature property map using the change in the spin phase of the fluid. In some embodiments there may be a temperature sensor to measure the temperature of the fluid to make the correction more accurate. This may account for drifts in both the magnetic field of the magnetic resonance imaging system and also for drifts in the temperature of the fluid of the fluid cooling system.

In another embodiment execution of the instructions further cause the processor to adjust the size and/or location of the sub-zones and/or the transducer position after starting to maintain the target zone at the target temperature. This embodiment may be beneficial because the sub-zones which were created may not have been optimum for the particular heating of the target zone. Adjusting the volume and location of the sub-zones may enable more efficient or accurate heating of the target zone.

In another embodiment execution of the instructions further cause the processor to heat the target zone while changing the selected sub-zone. In this embodiment the ultrasound transducer is moved from location to location when changing the sub-zone. It may be efficient to use the ultrasound transducer to heat the target zone while the ultrasound transducer is being moved from one location to another location.

In another embodiment a decision tree algorithm is used to initiate changing the selected sub-zone. This may be an efficient and simple way of providing for determining when sub-zone should be changed or even to select which sub-zone will be heated next.

In another embodiment the target temperature is any one of the following: between 38° C. and 40° C., between 39° C. and 40° C., between 40° C. and 45° C., between 40° C. and 44° C., between 40° C. and 43° C., between 40° C. and 42° C., between 40° C. and 41° C., between 41° C. and 45° C., between 41° C. and 44° C., between 41° C. and 43° C., between 41° C. and 42° C., between 42° C. and 45° C., between 42° C. and 44° C., between 42° C. and 43° C., between 43° C. and 45° C., between 43° C. and 44° C., between 44° C. and 45° C., between 38° C. and 39° C., between 52° C. and 55° C., greater than or equal to 55° C., and between 50° C. and 55° C.

In another aspect the invention provides for a computer program product comprising machine-executable instructions for execution by a processor controlling the medical instrument which comprises a magnetic resonance imaging system for acquiring magnetic resonance thermometry data from a subject within an imaging zone. The medical instrument further comprises a high-intensity focused ultrasound system comprising an ultrasound transducer with an electronically controllable focus. The high-intensity focused ultrasound system further comprises a mechanical positioning system for positioning the ultrasound transducer. The electronically controllable focus is operable to adjust the focus within the focusing zone. The location of the focusing zone is depending upon the position of the ultrasound transducer. Execution of the instructions causes the processor to receive a target zone descriptive of a volume within the subject. The target zone is larger than the focusing zone. Execution of the instructions further causes the processor to divide the target zone into multiple sub-zones. The sub-zones are divided into regions.

Each of the multiple sub-zones has a transducer position. When the transducer is at the transducer position the focusing zone comprises the sub-zone. Execution of the instructions further cause the processor to determine a sequence for moving the transducer position to each of the multiple sub-zones.

Execution of the instructions further cause the processor to determine a selected sub-zone selected from the multiple sub-zones using the sequence. Execution of the instructions further cause the processor to maintain the target zone at a target temperature for a predetermined duration by repeatedly controlling the mechanical positioning system to move the transducer to the transducer position of a selected sub-zone. An execution of the instructions further causes the processor to maintain the target zone at the target temperature for the predetermined time duration by repeatedly acquiring a magnetic resonance thermometry data using the magnetic resonance imaging system. The magnetic resonance thermometry data is descriptive of the temperature of the voxels in the sub-zone.

Execution of the instructions further causes the processor to maintain the target zone at the target temperature for the predetermined time duration by repeatedly determining a temperature property map descriptive of the temperature in each of the voxels using at least the magnetic resonance thermometry data. Execution of the instructions further causes the processor to maintain the target zone at the target temperature for the predetermined time duration by repeatedly heating each region independently to the target temperature by controlling the electronically controllable focus with a temperature feedback algorithm that uses the temperature property map. Execution of the instructions further cause the processor to maintain the target zone at the target temperature for the predetermined time duration by repeatedly changing the selected sub-zone using the sequence.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
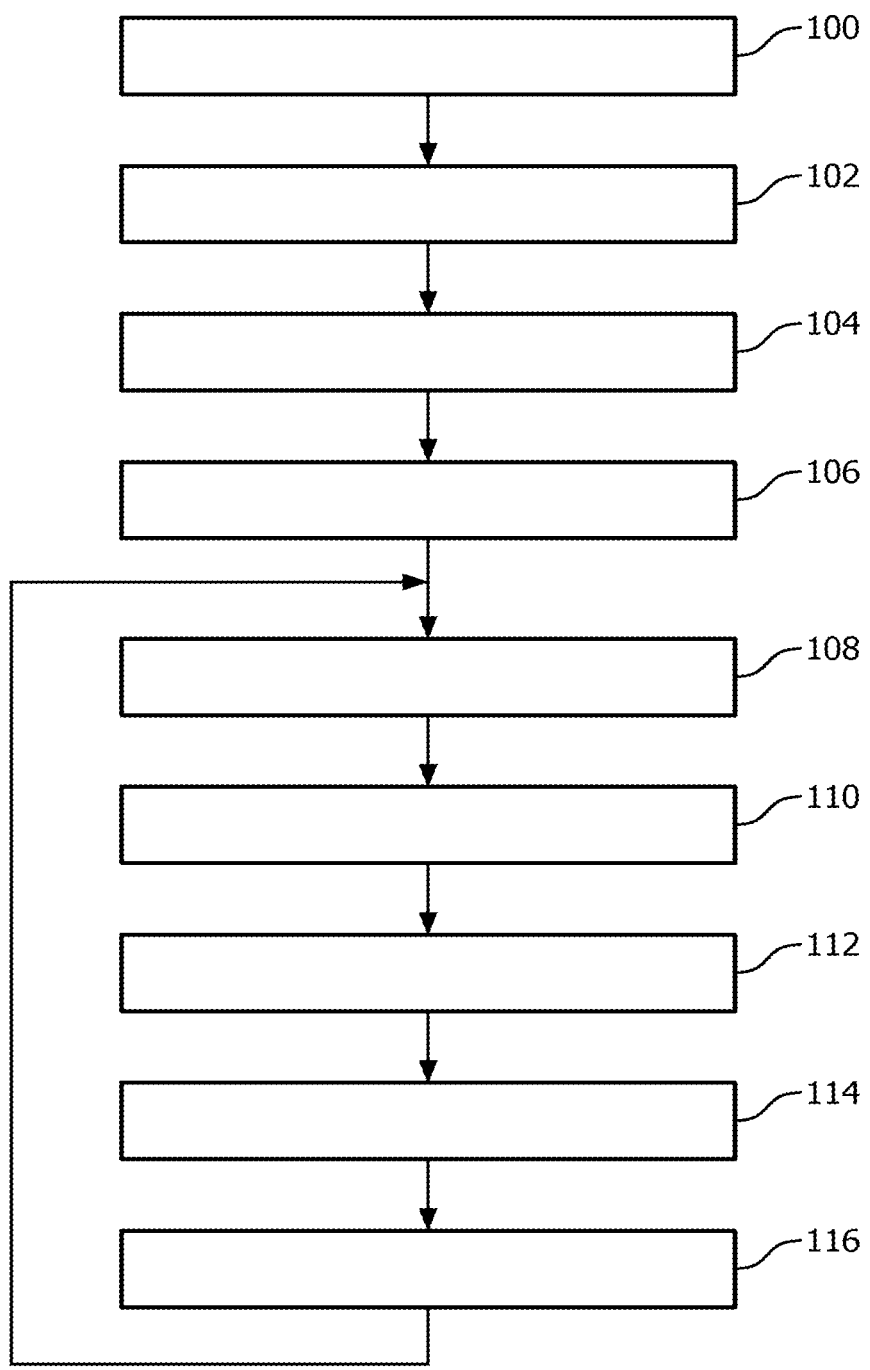
FIG. 1 shows a flowchart which illustrates an example of a method for controlling a medical instrument.

FIG. 1 shows a flowchart which illustrates an example of a method for controlling a medical instrument. In step 100 a target zone as received which is descriptive of a volume within the subject. Next in step 102 the target zone is divided into multiple sub-zones. Each of the multiple sub-zones has a transducer position associated with it. The target zone is larger than the size of the focus zone. When the transducer is at the transducer position a particular focusing zone comprises the associated sub-zone. Next in step 104 a sequence for moving the transducer position to each of the multiple sub-zones is determined. Next in step 106 a selected sub-zone is selected from the multiple sub-zones using the sequence.

Next step 108 is to control the mechanical positioning system to move the transducer to the position of the selected sub-zone. Next in step 110 magnetic resonance thermometry data is acquired. The magnetic resonance thermometry data is descriptive of the temperature of voxels in the sub-zone. Next in step 112 a temperature property map is determined or calculated which is descriptive of the temperature in each of the voxels using at least the magnetic resonance thermometry data. Next in step 114 each region is heated independently to the target temperature by controlling the electronically controlled focus with the temperature feedback algorithm that uses the temperature property map. Finally in step 116 the selected sub-zone is changed using the sequence. The method may go back to step 108, 110, 112, 114 or 116 and the process may be repeatedly performed until the heating procedure is finished. For instance for the duration of the predetermined time the method between steps 108 and 116 may be repeated.

Figure 2:
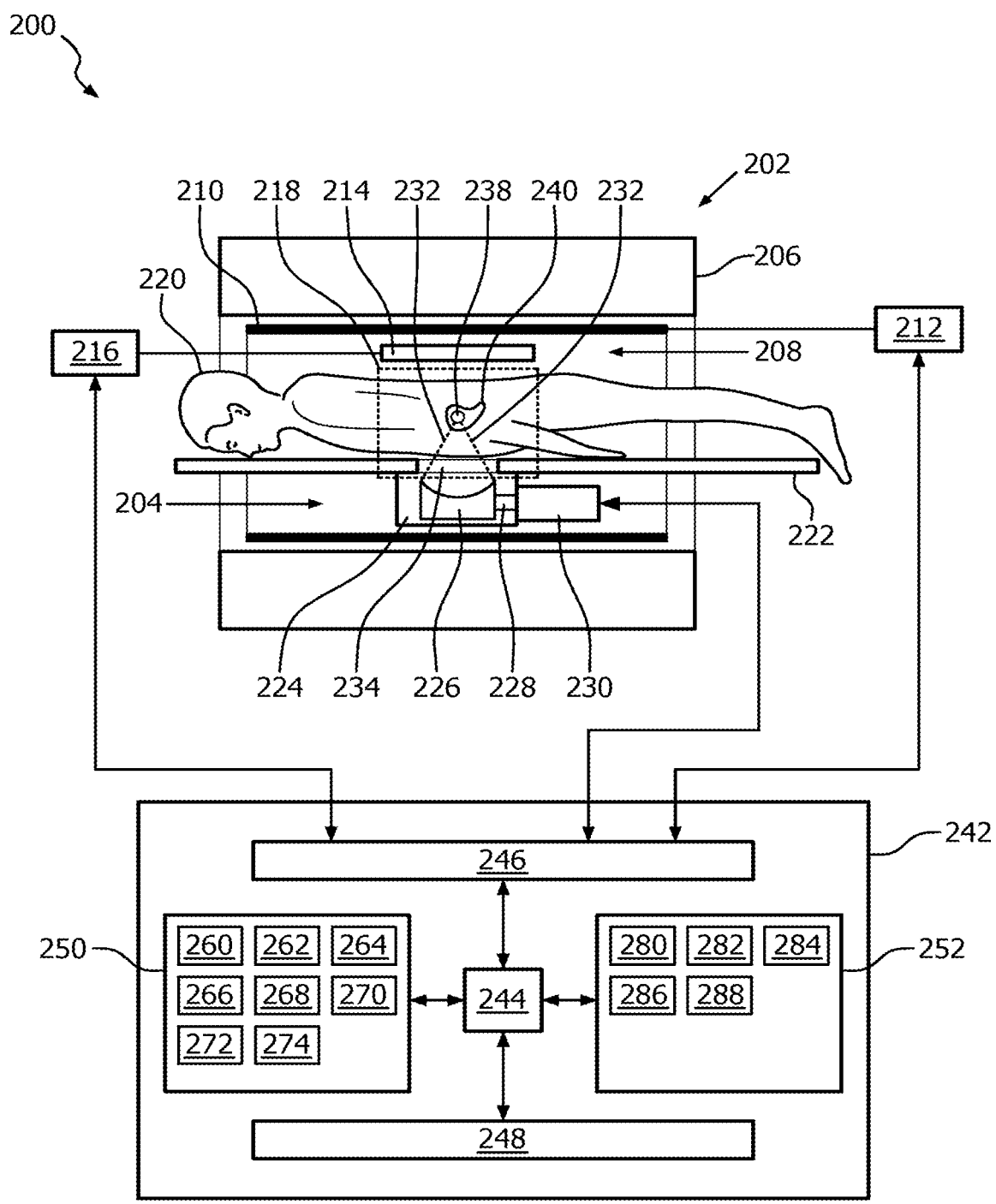
FIG. 2 shows an example of a medical instrument.

FIG. 2 shows an example of a medical instrument 200. The medical instrument comprises a magnetic resonance imaging system 202 and a high-intensity focused ultrasound system 204. The magnetic resonance imaging system comprises a magnet 206. The magnet shown in FIG. 2 is a cylindrical type superconducting magnet. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 208 of the cylindrical magnet 206 there is an imaging zone where the magnetic field is strong and uniform enough to perform magnetic resonance imaging.

Within the bore 206 of the magnet there is also a magnetic field gradient coil 210 which is used to spatially encode magnetic spins within an imaging zone of the magnet during the acquisition of magnetic resonance data. The magnetic field gradient coil 210 is connected to a magnetic field gradient coil power supply 212. The magnetic field gradient coil is intended to be representative. Typically magnetic field gradient coils contain three separate sets of coils for spatially encoding in three orthogonal spatial directions. A magnetic field gradient power supply supplies current to the magnetic field gradient coils. The current supplied to the magnetic field coils is controlled as a function of time and may be ramped or pulsed.

In the center of the bore 208 is an imaging zone 218. Adjacent to the imaging zone is a radio-frequency coil 214 which is connected to transceiver 216. Also within the bore 208 is a subject 220 reposing on a subject support 222. The radio-frequency coil 214 is adapted for manipulating the orientations of magnetic spins within the imaging zone and for receiving radio transmissions from spins also within the imaging zone. The radio-frequency coil 214 may contain multiple coil elements. The radio-frequency coil may also be referred to as a channel or an antenna. The radio-frequency coil 214 and radio frequency transceiver 216 may be replaced by separate transmit and receive coils and a separate transmitter and receiver. It is understood that the radio-frequency coil 214 and the radio frequency transceiver 216 are representative. The radio-frequency coil 214 is intended to also represent a dedicated transmit antenna and a dedicated receive antenna. Likewise the transceiver may also represent a separate transmitter and receivers.

The high-intensity focused ultrasound system 204 comprises a fluid-filled chamber 224 which houses an ultrasound transducer 226. The ultrasound transducer 226 is mechanically positioned by a mechanical positioning system 228. There is an actuator 230 for actuating the mechanical positioning system. In alternative embodiments the ultrasound transducer may be a manually positioned external transducer without the fluid-filled chamber 924 or mechanical positioning system 228.

The ultrasonic transducer 226 may also contain multiple elements for emitting ultrasound. A power supply which is not shown may control the amplitude and/or phase and/or frequency of alternating current electric power supplied to the elements of the ultrasonic transducer 226. The dashed lines 232 show the path of ultrasound from the ultrasonic transducer 226. The ultrasound 232 first passes through the fluid-filled chamber 224. The ultrasound then passes through an ultrasound window 234. After passing through the ultrasound window 234 the ultrasound passes through an optional gel pad 236 or a layer of ultrasound conductive gel which may be used to conduct ultrasound between the window 234 and the subject 220. The ultrasound 232 then enters the subject 220 and is focused into a focus 238 or sonication point. There is a region 240 which is a target zone. Through a combination of electronic and mechanical positioning of the focus 238 the entire target zone 240 can be heated. The target zone 240 is within the imaging zone 218. The high-intensity focused ultrasound system 204, the transceiver 216, and the magnetic field gradient coil power supply 212 are all connected to a hardware interface 246 of computer system 242. The hardware interface 246 is connected to processor 244. The processor 244 is also connected to a user interface 248, computer storage 250, and computer memory 252.

The computer storage 250 is shown as containing focusing zone definition data 260. The focusing zone definition 260 is data which is used to define the size of the focusing zone 238. The focusing zone may be defined in terms of an area above which the intensity of the ultrasound is above a threshold or it may be defined in terms of fixed coordinates which may be defined relative to the position of the ultrasound transducer 226 or may be dependent upon the coordinates set by the mechanical positioning system 228. The computer storage 250 is further shown as containing a target zone coordinates 262. The target zone coordinates 262 contain data which identify the location of the target zone 240. The target zone coordinates 262 may in some embodiments be absolute coordinate definitions or in other embodiments may be defined in terms of their position relative to anatomical landmarks of the subject 220.

The computer storage 250 is further shown as showing sub-zone coordinates 264. The sub-zone coordinates 264 contain coordinates which divide the target zone into the respective sub-zones. The computer storage 250 is further shown as containing transducer position coordinates 266. There is a transducer position coordinate 266 for each of the sub-zones. The computer storage 268 is further shown as containing a pulse sequence 268. The pulse sequence is a set of commands which the processor 244 is able to issue to the magnetic resonance imaging system 202 to acquire magnetic resonance data. The pulse sequence 268 may contain a pulse sequence which is designed to acquire magnetic resonance thermometry data. The computer storage 250 is further shown as containing magnetic resonance thermometry data 270 that was acquired using the pulse sequence 268. The computer storage 250 is further shown as containing a sequence 272. The sequence 272 contains a sequence of sub-zones to be heated. This may be a predefined list or it may be an initial sub-zone and the rest may be developed or modified on the fly. The computer storage 250 is further shown as containing a temperature property map 274 which was reconstructed from the magnetic resonance thermometry data 270.

The computer memory 252 is shown as containing a control module 280. The control module 280 contains computer-executable code which enables the processor 244 to control the operation and function of the medical instrument 200. The computer memory 252 is further shown as containing a sub-zone division module 282. The sub-zone division module 282 contains computer-executable code which enables the processor 244 to divide the target zone coordinates 262 into a set of sub-zone coordinates 264 and also may calculate the transducer position coordinates 266 at the same time. The computer memory 252 is further shown as containing an image reconstruction module 284. The image reconstruction module 284 enables the processor 244 to construct the temperature property map 274 from the magnetic resonance thermometry data 270. The image reconstruction module 284 in some embodiments may also be able to reconstruct other magnetic resonance data or images from the magnetic resonance data 270.

The computer memory 252 is further shown as containing a temperature control algorithm 286 which enables the processor 244 to control the high-intensity focused ultrasound system 204 to maintain the temperature within a selected sub-zone by analyzing the temperature property map 274 on a voxel-based basis. The computer memory 252 is further shown as containing a sub-zone selection algorithm 288. The sub-zone selection algorithm 288 enables the processor 244 to use the magnetic resonance thermometry data 270 and/or the temperature property map 274 to select the next sub-zone to be heated.

Figure 9:
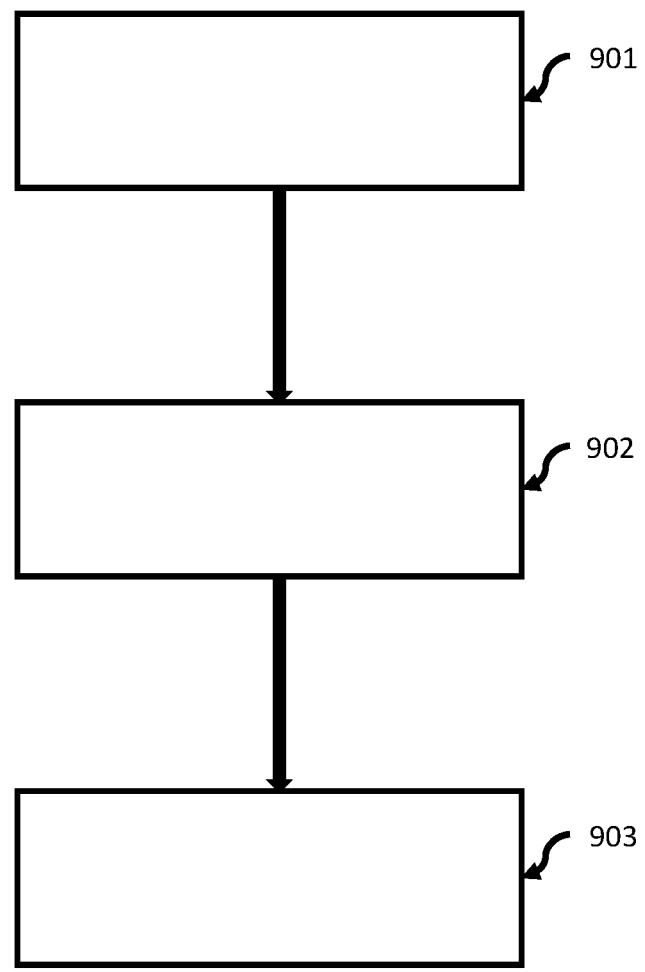
FIG. 9 shows a flowchart of further steps that may be performed by the processor.

In an embodiment, execution of the instructions further causes the processor to: determine a temperature property for each of the multiple sub-zones using the magnetic resonance thermometry data (FIG. 9, step 901); select a next sub-zone using the temperature property for each of the multiple sub-zones (FIG. 9, step 902); and modify the sequence such that the next sub-zone is sequentially next in the sequence (FIG. 9, step 903).

Figure 3:
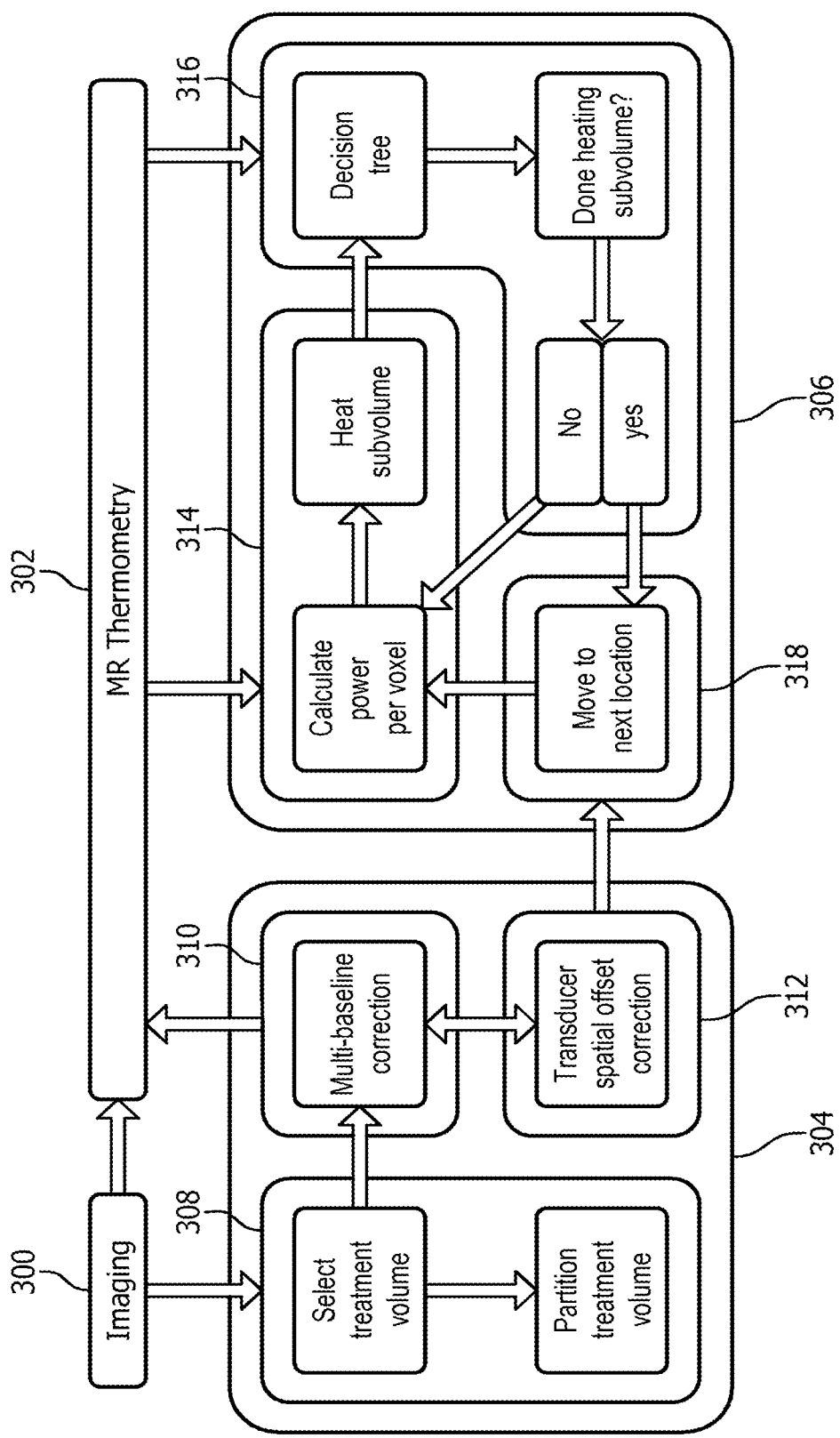
FIG. 3 shows a flowchart which illustrates a method for conformal heating a large volume for hyperthermia.

FIG. 3 shows a flowchart which illustrates a method for conformal heating a large volume for hyperthermia. The flowchart in FIG. 3 is broken into four main parts: 300 represents imaging, 302 represents magnetic resonance thermometry using imaging data, 304 is a treatment planning module, and 306 is sonication feedback cycle 306. The imaging 300 provides data to a treatment planning module 304 and the MR thermometry 302. The treatment planning portion 304 comprises several sub-steps. One is a treatment zone partitioning algorithm 308. The treatment zone partitioning algorithm 308 is able to select the treatment zone and also partition into sub-zones. This information is then fed into block 310 which represents a multi-baseline correction. Block 304 also contains a transducer spatial offset correction. This provides data to the multi-baseline correction 310 and also to the sonication-feedback cycle 306. The multi-baseline correction 310 also provides data useful for the magnetic resonance thermometry 302. The sonication-feedback cycle 306 receives the magnetic resonance thermometry data which is used for calculating temperature feedback control 314. This is done by calculating the power per voxel calculating how much heat to provide each sub-zone. This data is then used by a decision tree 316 which uses the information from the temperature feedback control 316 and the magnetic resonance thermometry 302. The decision tree 316 decides to continue heating the current sub-zone or to move to the next location. Block 318 indicates moving to the next location. The location 318 may be adjusted by the transducer spatial offset correction 312. After moving to the next location 318 the temperature feedback control portion 314 is repeated. The steps in block 306 are repeated until the heating is completely finished.

Mild hyperthermia (40-45° C.) has demonstrated an ability to improve the effectiveness of anticancer therapies such as chemotherapy and radiation in pre-clinical and clinical studies. Temperatures below mild hyperthermia may not have the desired effect, while temperatures above this range may stop tissue perfusion, negatively impacting drug delivery or radiation therapy. Parameters that are critical to achieving adequate mild hyperthermia treatments include thermal dose, target temperature, spatial accuracy, temperature stability and duration. In order to control these parameters, a number of hyperthermia applicators have been used for both deep-tissue and topical hyperthermia, including contact heating, microwave, radio frequency and ultrasound.

The narrow, 40-45° C. range of mild hyperthermia temperatures requires tight control of temperature with a feedback mechanism. MR-guided high-intensity focused ultrasound (MR-HIFU) has the ability to provide such feedback noninvasively using proton resonance frequency shift (PRFS) thermometry. MR-HIFU is capable of heating tissue using either electronic or mechanical steering. Electronic steering involves deflection of the focal point by varying phases of acoustic waves generated by each of the transducer elements while mechanical steering is achieved through translation and/or rotation of the transducer. Each method of steering has significant limitations: electronic steering is limited to small deflections (~8 mm) [1], and mechanical steering interferes with temperature imaging using the PRFS method, with larger displacements resulting in more noise, but is also significantly slower [2]. These shortcomings of the current heating approaches have so far limited application of MR-HIFU in mild hyperthermia, despite initial positive results in the clinic [3].

One of the most significant drawbacks that arise from the above limitations is the small size of the target volume (1-2 cc) that MR-HIFU has been used to heat to mild hyperthermia [2]. Ablation of large volumes of tissue has been achieved through fast sequential complete ablation of small volumes [1]. However, such piecewise heating is not appropriate for mild hyperthermia treatment of large volumes, since it is required to heat the entire volume continuously for a prolonged period of time (30-60 min) for applications with radiation or drug delivery. Most hyperthermia algorithms require a predefined treatment shape, such as a circle, and are thus not conformal to a tumor [1, 2, 4]. This limitation on treatment volume shape is not well suited for the clinic, where it is desirable to avoid heating healthy tissue and critical/vulnerable structures such as blood vessels. Finally, tumor tissue is heterogeneous (perfusion and absorption of energy), meaning that the power required to heat different regions depends on local tissue properties. This heterogeneous nature of tumor tissue calls for voxel/region-based feedback. Thus, three problems must be addressed for clinical translation of mild hyperthermia with MR-HIFU: 1) heating of large volumes, 2) conformal heating, 3) heating of heterogeneous tissue.

To address these challenges, the comprehensive approach to mild hyperthermia in this disclosure includes an algorithm that combines electronic and mechanical steering, in order to heat large volumes. This combination was made possible by a divide-and-conquer approach, which was used to partition the treatment volume into subvolumes and a decision tree algorithm architecture that allowed for real-time adaptation of the treatment to ensure heating across all subvolumes. Size of these subvolumes was determined by the maximum volume reachable with electronic steering alone. Voxel/region-based feedback was implemented to achieve homogeneous heating or the desired treatment volume, and multi-baseline thermometry was used to account for transducer motion and provide temperature feedback during treatment. The proposed algorithm was implemented on a clinical Philips Healthcare Sonalleve MR-HIFU platform.

Thermal ablation requires temperature to be raised to a level capable of inducing necrosis (usually >55° C.) for a short duration (seconds), whereas mild hyperthermia requires that temperature in the target region be maintained at a desired level for a prolonged duration. Since the optimum temperature for most mild hyperthermia applications is in the 40-45° C. range (T<40° C. causes limited effect, T>45° C. may shut down tissue perfusion), an approach that is completely different from ablation is required for mild hyperthermia. This may provide a flexible algorithm architecture that is capable of real-time adaptation during treatment, in that both the subvolume shape and the power with which each voxel is heated can be automatically adjusted in real-time. Embodiments may provides a reduction to practice, framework and characterization of the algorithm to demonstrate the combination of electronic and mechanical steering, with capability for real-time updates (not previously disclosed) and support for any feedback algorithm, including but not limited to binary, proportional-integral, and proportional-integral-derivative. This approach offers a concrete way to minimize the mechanical movement of the transducer, thus improving the stability of heating in cases where heating during transducer movement is not possible. Compared to known binary ablation feedback and mild hyperthermia feedback algorithms and other published and/or patented work, embodiments may offer significant improvements and additional features for large volume partitioning, feedback control methods and maintenance of mild hyperthermia in volumes greater than those reachable using electronic steering alone. Embodiments may yield a conformal, large volume, and homogeneous temperature distribution deep in tissue that is required for most clinical applications. This homogeneous temperature distribution is achieved by voxel/region-wise feedback, volume partitioning, electronic and mechanical steering, decision tree and multi-baseline MR thermometry.

The essential features of this invention may include volume partitioning, decision tree, electronic and mechanical steering, voxel/region-wise feedback and multi-baseline MR thermometry. These features are discussed in detail below.

Conformal Large Volume Hyperthermia Algorithm

The conformal large volume hyperthermia algorithm uses a series of steps to plan the treatment, acquire information needed to begin treatment (i.e. baseline temperature, various correction factors), and to perform the heating. These steps are shown in FIG. 3 and addressed below in greater detail.

In FIG. 3. Conformal large volume hyperthermia algorithm flowchart. During treatment planning, a treatment volume was selected and partitioned into subvolumes using the treatment volume partitioning algorithm. At each of the transducer locations provided by the algorithm, multi-baseline collection and transducer spatial offset collection were performed. Multi-baseline collection was then repeated using the collected spatial offsets. During the sonication, both multi-baseline correction and transducer spatial offset correction were used. With each dynamic MR image (1.6 s), a decision tree was used to determine whether to heat the current subvolume and, if the decision to move was made, to determine the next location/subvolume for heating. Proportional feedback control was used to calculate a map of power with which the current subvolume was heated using electronic steering. This feedback loop was repeated until the user-defined sonication time had elapsed.

Figure 4:
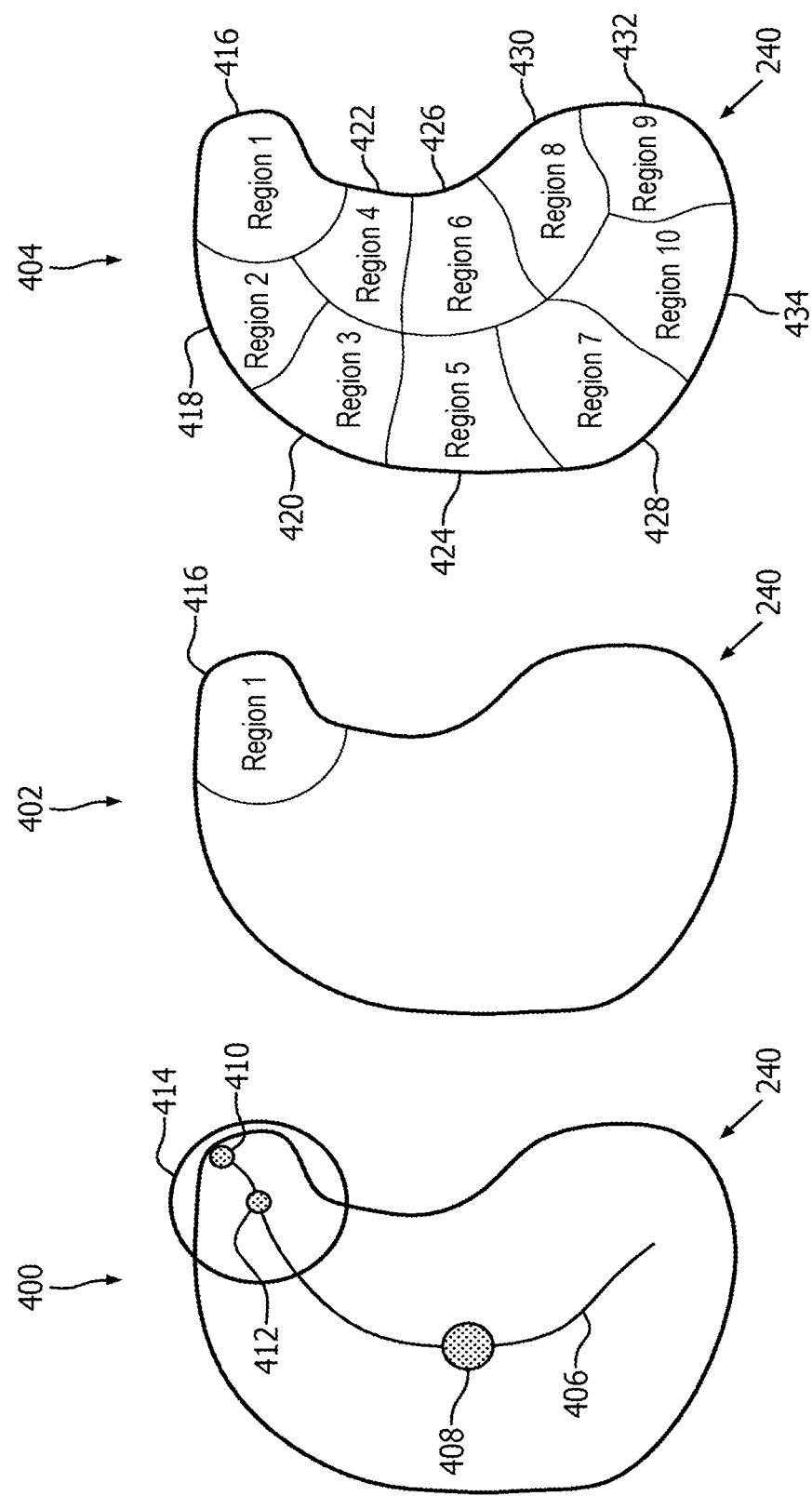
FIG. 4 illustrates a method of dividing a target zone into sub-zones.

Target Volume Partitioning Approach:

A user-defined, free-hand-drawn target volume is automatically divided into subvolumes using a divide-and-conquer algorithm (cf. FIG. 4). Each of the subvolumes would be heated using electronic steering of the HIFU focal spot, whereas mechanical translation of the HIFU transducer can be used to position the transducer at the appropriate position to heat each subvolume. Size of individual subvolumes is limited to the volume that can be adequately covered with electronic steering alone (user defined). Subvolume size can vary, but it is typically limited by electronic steering capability of the transducer to ensure optimal focusing, adequate acoustic intensity, and definition of the border of the heated region (conformal heating). This approach is applicable to both 2D and 3D volume partitioning.

FIG. 4 illustrates a method dividing a target zone into sub-volumes. There is a target zone 240. There are three views 400, 402, 404 which show the target zone 240. FIG. 4 illustrates the medial axial method. A medial axis or skeleton is calculated. This is indicated by the line 406. The center of mass 408 of the target zone 240 is then located. The large dot 408 represents the approximate location of the center of mass. Next along the medial axis 406 the voxel 410 furthest from the center of mass is located. Next along the medial axis 406 a focus point 412 is chosen. The focus point 412 is the natural unadjusted focus point of the ultrasonic transducer and is positioned such that the maximum amount of the target zone 240 is within the bounds of the focusing 414 and also the voxel 410. This then defines the first sub-region 416. View 402 shows the location of region 416 relative to the target zone 240. The target zone 240, not including the region 416, then repeats the process illustrated in view 400. This is done repeatedly until the entire target zone 240 is divided into sub-zones. View 404 shows the target zone 240 divided into ten sub-volumes. These are labeled 416, 418, 420, 422, 424, 426, 428, 430, 432, and 434.

FIG. 4 illustrates a volume segmentation algorithm. Following calculation of the skeleton 406, the farthest voxel 410 from the center of mass (CoM) 408 is found and the skeleton is extended to the farthest voxel 410. After finding the optimal focal location 412 along the extended skeleton, volume that can be reached from the focal point are labeled. These steps are repeated until the entire volume is divided into subvolumes, each uniquely labeled.

The treatment volume partitioning algorithm described below results in 1) a treatment volume partitioned into subvolumes and 2) a list of natural, non-deflected HIFU focus locations in these subvolumes from which all voxels within a given subvolume can be reached using electronic steering (called transducer locations herein). Note that each natural HIFU focus location corresponds to a physical transducer location.

The algorithm partitions a treatment volume using a medial axis transformation (skeletonisation), which contains information about the shape of the treatment volume. This skeletonization is used to find transducer locations, while maximizing their associated subvolume size. This process minimizes the total number of transducer locations, decreasing the total travel time of the HIFU transducer during treatment. Decreasing the mechanical movement of the transducer has the benefit of limiting possible interference with MR thermometry, increasing the stability of heating in cases where heating is not possible during movement (as in disconnected regions), limiting equipment maintenance costs, and perhaps most importantly, increasing patient comfort and increasing clinical throughput. Finally, the algorithm associates each transducer location with the voxels that can be heated from this location using electronic steering alone.

An example of the treatment volume partitioning algorithm workflow:

1. Calculate a Euclidean distance transform (DT) from treatment volume centroid.
2. Perform a skeletonisation of the treatment volume.
3. Select the voxel with the highest DT value within the treatment volume (the starting voxel).
4. Extend the skeleton linearly to the starting voxel.
5. Place the center of the electronic steering volume in the starting voxel and calculate the overlap with the treatment volume (consider only voxels not already assigned to any subvolume).
6. Repeat the previous calculation by placing the center of the electronic steering volume at every voxel along the extended skeleton, which is at a distance to the starting voxel≤radius of the electronic deflection.
7. Determine the voxel at which the treatment volume and electronic steering volume have greatest overlap. If multiple voxels are selected, choose the voxel furthest from the boundary of the treatment volume.
8. Add the selected voxel to the set of transducer locations.
9. Label all the voxels that can be reached with electronic steering from the transducer location under consideration. If voxels which have been labeled already are required to be labeled again in this step, choose the label of the transducer location that is nearest to these voxels. Voxels outside the treatment volume remain unlabeled.
10. Repeat steps 2-9 until all voxels in the treatment volume have been labeled.

Multi-Baseline MR Thermometry and Focal Spot Spatial Offset Correction:

Treatment volume selection and partitioning: A multi-slice 2D or a 3D MR image stack can be used to select a treatment volume (FIG. 5, 'Treatment planning', treatment planning 308). This volume is partitioned into subvolumes using the treatment volume partitioning algorithm described above (FIG. 4).

Multi-baseline thermometry with multiple transducer locations: During multi-baseline collection MR phase images were acquired in every transducer location (FIG. 3, 'Treatment planning', Treatment Planning 310). These were substituted as baseline images into the temperature calculation at the appropriate transducer locations in real-time. This procedure allows for stable temperature mapping without the effect of transducer position on phase/temperature images. During this step, a geometric relationship between the transducer and the focal spot locations can be used. The next step ('spatial offset correction') will measure and apply correction factors that ensure accurate positioning, necessitating repetition of baseline temperature collection before beginning treatment. Note, that multi-baseline has been used/published in the past to correct for patient or target volume movement. The approach described herein is to account for transducer movement (we do not know if this concept is prior art). Alternative means to correct the effect of transducer position to phase/temperature images, such as modeling of transducer phase effect, should be included in the scope of the invention.

Spatial offset correction: Optional spatial offset correction can be performed for one or more transducer positions to correct actual heating location. After starting MR thermometry, low power test sonications can be performed at each of the transducer positions calculated during volume partitioning (FIG. 3, Treatment Planning Step 312). The positions heated with the low power sonications can be determined from MR thermometry by finding the locations of highest temperature reached or greatest change in temperature relative to baseline, among other methods. An automatic algorithm is used to perform the search for the focal spot locations in a neighborhood around the treatment volume that excludes areas where MR thermometry is inaccurate (bowel, moving organs). The algorithm can examine multiple slices in its search for the focal spots. Focal spot spatial offsets for each of the transducer locations (each corresponds to a subvolume) are then determined by relating the geometrically calculated natural focus spot locations to the detected locations. This set of 3D spatial offsets can thereafter be used to correct for transducer motion. Following the acquisition of spatial offsets, a multi-baseline collection can be repeated in order to gather baseline temperature at corrected transducer locations, using the acquired spatial offsets (FIG. 3, Treatment Planning Step 310).

Figure 5:
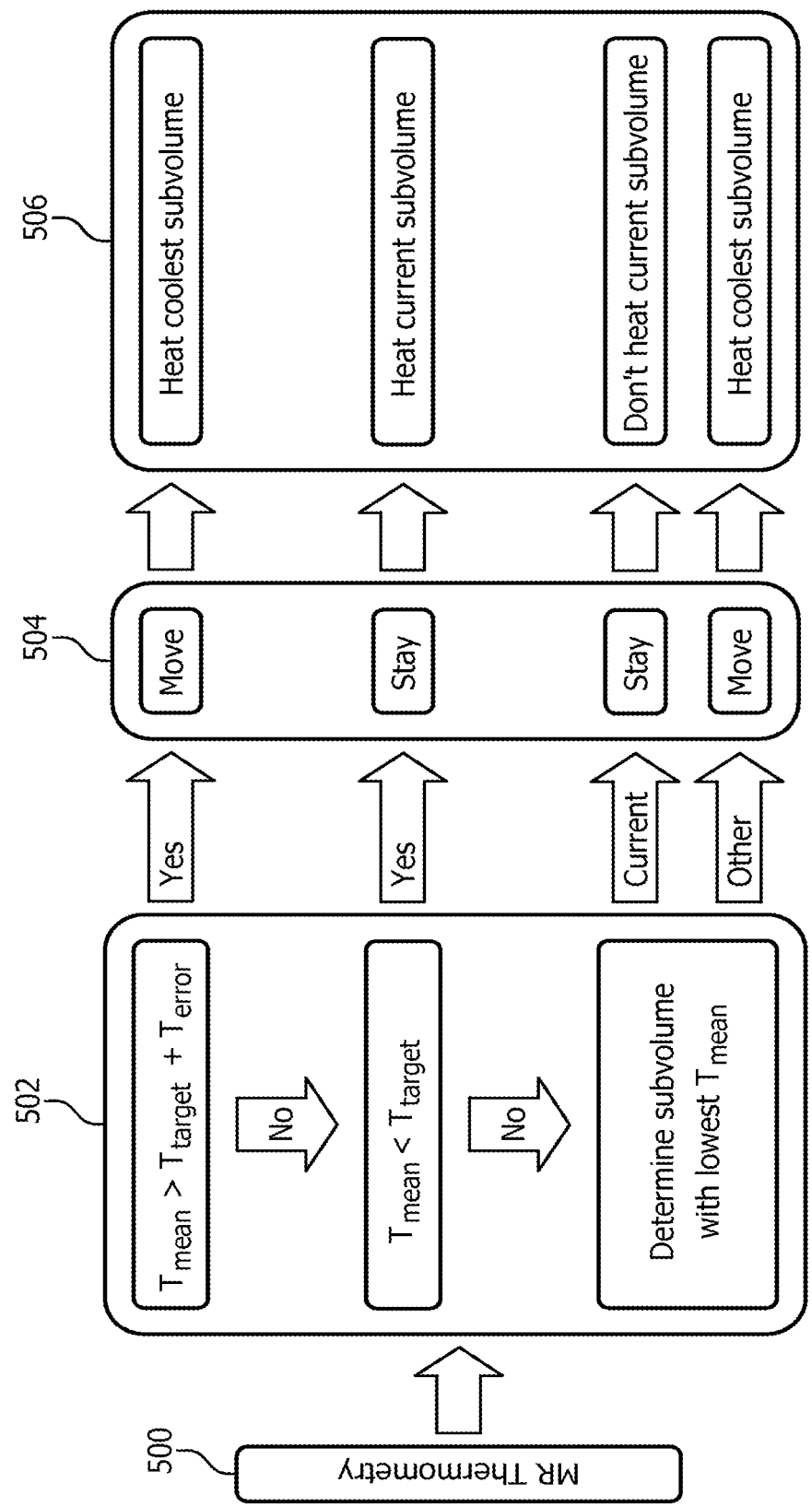
FIG. 5 shows a flowchart which illustrates an example of a decision tree used for deciding which sub-zone or sub-volume to heat.

FIG. 5 shows a flowchart which illustrates an example of a decision tree used for deciding which sub-zone or subvolume to heat. There is a block which represents the acquisition of magnetic resonance thermometry data 500 which is then fed into a tree which evaluates a particular temperature condition 502 using a conditional test. The block 504 represents the result of the test and 506 indicates which sub-volume or sub-zone is heated. After the magnetic resonance thermometry data has been acquired there is then a decision tree in block 502. For instance the mean temperature could be compared to the target temperature plus its error. If the temperature is above this mean then a decision may be made to move the transducer to a new location for instance to heat the coolest sub-volume. If the mean is not above the target plus its error value then the mean may be compared to the target. If the mean is less than the target then a decision may be made to stay and heat the current sub-volume. If the mean is less than the target for instance a decision may be made to determine the sub-volume with the lowest mean temperature. If this is the current sub-volume then the transducer may stay in the same location. If the temperature with the lowest mean temperature is another location a decision may be made to move and heat the coolest sub-volume.

FIG. 5. Decision tree used during sonication. This algorithm results in heating of the current subvolume if its mean temperature ($T_{mean}$) is below the target temperature ($T_{target}$) and if the current subvolume has the lowest $T_{mean}$. In other cases, this algorithm directs the transducer to move to the subvolume with the lowest $T_{mean}$.

Decision Tree:

The large volume, conformal heating algorithm uses a decision tree to determine whether to continue heating or to mechanically move to another subvolume (FIG. 3, Sonication—Feedback Cycle, Step 316 and FIG. 5).

Figure 6:
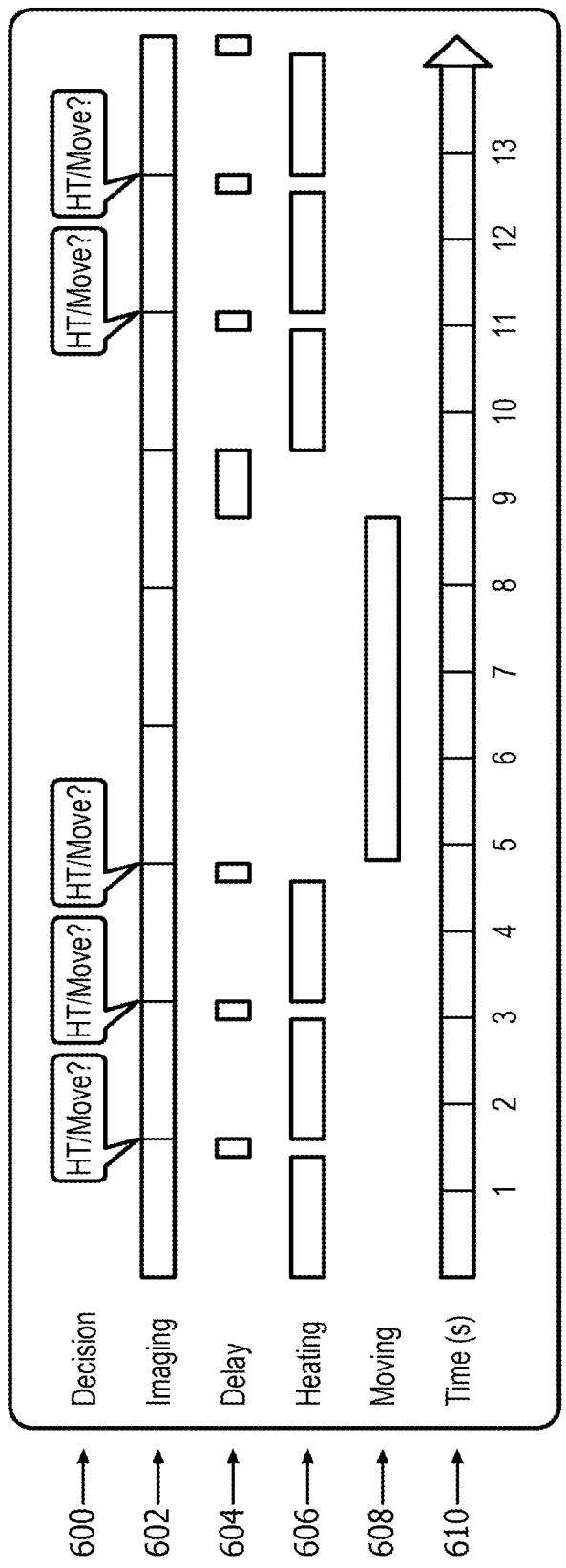
FIG. 6 shows an example timeline which indicates the movement and sonication during use of a medical instrument.

FIG. 6 shows an example of a timeline which indicates the movement and sonication during use of the medical instrument. The dashed in line 600 indicate a decision and this may be a decision to either heat or move the transducer. Next 602 indicates when magnetic resonance imaging takes place to acquire magnetic resonance thermometry data. In block 604 this shows when a delay is occurring. The delay occurs when a decision is made and also when the transducer is moved to a new location. 606 indicates when heating is performed. In some embodiments the heating may still be performed when moving is occurring. 608 shows when the transducer element is being moved. And 610 shows the time in arbitrary units.

If the current subvolume is found to be sufficiently heated, the decision tree determines the next subvolume that needs to be heated using a set of criteria that may include average, minimum, maximum or other measures. The decision tree is used with each dynamic image to ensure that most up-to-date temperature maps are used to make decisions. One example of an effective use of a decision tree (FIG. 5) resulted in the heating of the current subvolume if 1) overshoot greater than the error in temperature ($T_{error}$) had not occurred ($T_{error}$ can be measured directly from MR thermometry images); and 2) mean temperature ($T_{mean}$) of the subvolume was lower than target temperature. If one of these conditions was false, the decision tree directed the transducer to move to the subvolume with the lowest $T_{mean}$. If the subvolume with the lowest mean temperature was the current subvolume, a decision was made to stay for one feedback cycle duration, without heating. If the decision was made to heat a different subvolume, the HIFU transducer was moved to the associated transducer location. In either case of reheating the current subvolume, or moving to and heating the next suitable subvolume, the subvolume heating cycle was repeated. If the decision to stay at the current transducer location without reheating was made, the treatment volume was allowed to cool for one feedback cycle duration, at which point the temperature was evaluated. The algorithm depicted in FIG. 5 can be repeated until the user-defined sonication time elapses. A timing diagram of the various parts of the system working together is depicted in FIG. 6.

FIG. 6. Timeline of movement and sonication. The schematic represents an example of the timeline of movement and sonication, showing the points at which the decision tree was used (a), the imaging time (b), delay between commands issued by the algorithm (c), heating using electronic HIFU steering (d), mechanical transducer movement (e) and time (f).

Voxel/Region-Wise Feedback:

The use of a decision tree algorithm architecture allows for flexibility in the choice of temperature feedback algorithms since it limits temperature overshoot. Therefore, provided that maximum power is limited to avoid tissue damage (through mechanical effects such as cavitation), the choice of feedback algorithms includes, but is not limited to binary, proportional, proportional-integral and proportional-integral-derivative. Any of these algorithms can be used to prescribe power per voxel or for an arbitrarily defined region (e.g., 3×3×3 mm) within the target volume, based on MR-thermometry feedback from voxels or regions. Instead of power, the feedback algorithm may also adjust the sonication duration, duty cycle, or any other parameter, which affects the total output energy over time. In order to limit the influence of MR thermometry artifacts that result from transducer motion, temperature feedback control can base its power calculation on the latest accurate MR thermometry image acquired, after transducer motion has ceased. Voxel/region-wise feedback method for controlling the heating in a subregion is one method to enable subregion heating to the target temperature. However, the abovementioned multiple position heating and related methods can be combined with other heating algorithms, and the scope of the invention also includes alternative heating methods.

TABLE I

THERMAL EVALUATION FOR THE TREATMENT VOLUMES IN PHANTOM

| No. | No. of subvolumes | No. of voxels | Size (cm$^2$) | Heat-up time (min) | Mean T (° C.) | Mean SD (° C.) | T$_{10}$-T$_{90}$ (° C.) | Mean T$_{90}$ (° C.) | Mean T$_{10}$ (° C.) | Av max T (° C.) | Av min T (° C.) | Max T (° C.) |
|---|---|---|---|---|---|---|---|---|---|---|---|---|
| 1 | 2, linear | 73  | 1.9 | 1.3 | 41.1 | 0.5 | 1.3 | 40.5 | 41.7 | 42.0 | 40.0 | 42.6 |
| 2 | 3, linear | 141 | 3.8 | 2.0 | 41.0 | 0.5 | 1.4 | 40.4 | 41.8 | 42.2 | 39.8 | 42.8 |
| 3 | 4, linear | 138 | 3.7 | 2.8 | 40.9 | 0.5 | 1.4 | 40.3 | 41.6 | 42.1 | 39.4 | 42.9 |
| 4 | 4, bulky  | 148 | 3.9 | 2.4 | 41.0 | 0.5 | 1.3 | 40.4 | 41.7 | 42.0 | 39.8 | 42.3 |
| 5 | 6, bulky  | 257 | 6.8 | 3.4 | 40.7 | 0.5 | 1.4 | 40.0 | 41.5 | 42.0 | 39.3 | 42.6 |
| 6 | 9, bulky  | 331 | 8.8 | 5.5 | 40.8 | 0.4 | 1.2 | 40.3 | 41.5 | 42.0 | 39.5 | 42.6 |

For every treatment volume, numbers of subvolumes and voxels as well as size are reported. Furthermore, heat-up time is displayed, defined as the time at which every subvolume has reached a mean temperature greater than or equal to $T_{target}-T_{error}$. In addition, other thermal properties, such as mean temperature (Mean T), mean standard deviation (mean SD), T90-T10 ranges, Mean T90, Mean T10, average maximum and minimum temperatures (Av max and min T, respectively) and overall maximum temperatures after heat-up (Max T), are displayed. Averages or means were calculated by averaging values after heat-up until end of sonication.

Combination of Electronic and Mechanical Steering:

The use of electronic steering of the HIFU focal spot within each subvolume allows for precise heating of areas depicted by individual voxels, or small regions, depending on MR image resolution. As mentioned above in "Voxel/region-wise feedback," a feedback algorithm can be used to calculate the acoustic power with which each voxel/region is to be heated. Heating was achieved by electronically steering the focal point of the HIFU transducer over the current subvolume. Depending on the dynamic scanning time and the number of voxels to be heated, multiple sonications of the same voxel could occur. In this case, power for such voxels can be divided by the number of sonications in them. Heating of the subvolume was then performed for a duration equal to the number of heated voxels times the number of passes over each voxel times the voxel heating time. Electronic deflection along and perpendicular to the beam axis may diminish the realized intensity at the intended HIFU focus and change the location of maximal intensity. Therefore, for every voxel power can be adjusted using second order polynomial multiplier depending on the electronic deflection from the natural focal position.

Figure 7:
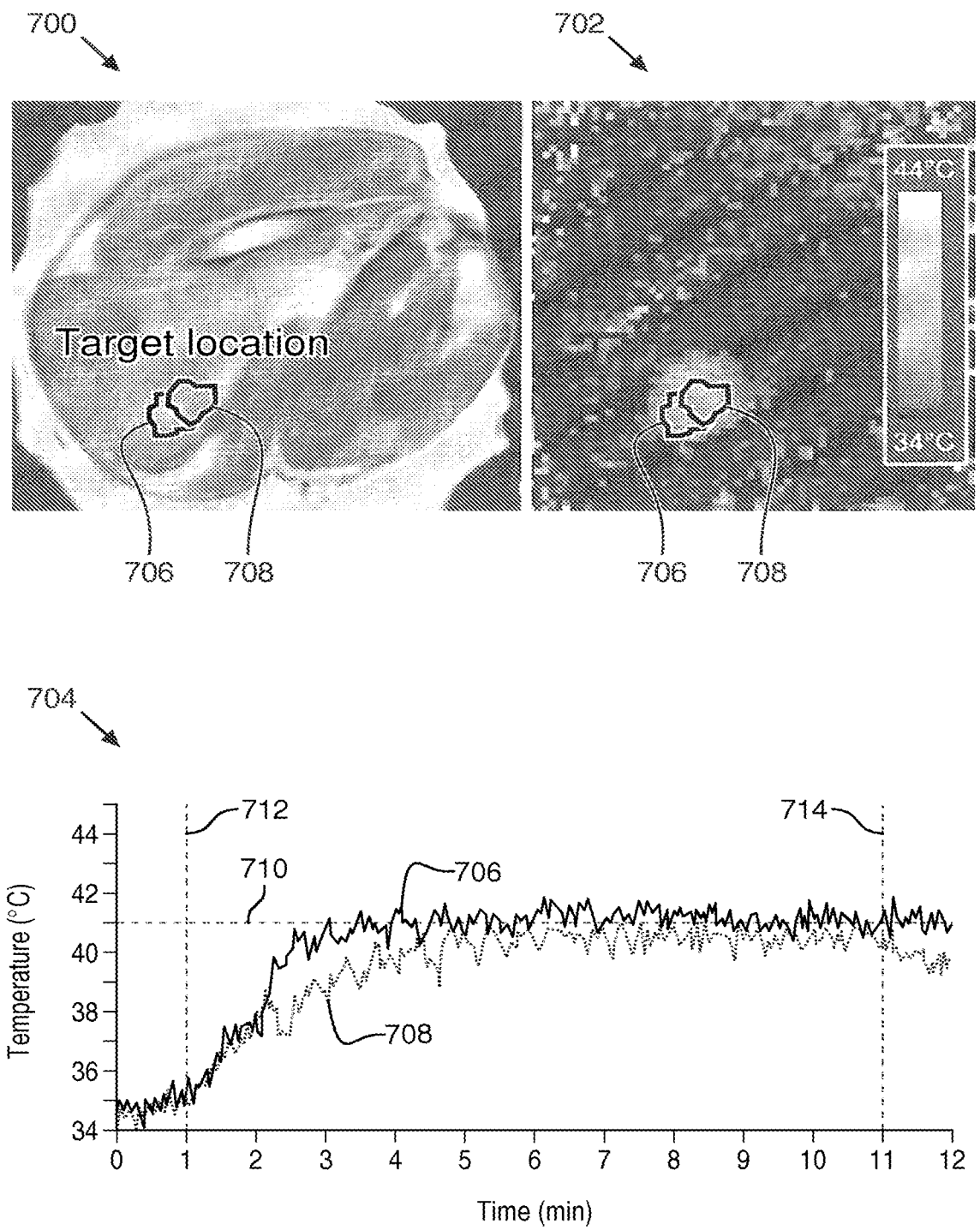
FIG. 7 demonstrates the application of a large area conformal heating method in vivo.

This data demonstrate that the system allows for fast heat-up and conformal, well-controlled heating. While the heat-up time does increase with increasing volume (1.3-5.5 min), this increase is small relative to a typical mild hyperthermia treatment of 1 hour. FIG. 7 demonstrates the performance of this algorithm in vivo, with performance similar to the phantom experiment.

This data demonstrate that the system allows for fast heat-up and conformal, well-controlled heating. While the heat-up time does increase with increasing volume (1.3-5.5 min), this increase is small relative to a typical mild hyperthermia treatment of 1 hour. FIG. 7 demonstrates the performance of this algorithm in vivo, with performance similar to the phantom experiment.

FIG. 7 shows two images 700, 702 and a chart 704. Image 700 is a planning image. Image 702 shows a thermal magnetic resonance image or a temperature map acquired immediately upon both sub-zones having a temperature average greater than 40° C. This shows conformal heating over the entire zone. In FIG. 700 the treatment different zone locations and its automatic partitions into sub-zones each of which can be treated with electronic focusing alone. In the plane image 700 can be seen two sub-zones. There is a first sub-zone 706 and a second sub-zone 708. These two sub-zones are also visible or marked in the thermal image 702. The chart 704 shows time in minutes versus the temperature in degrees Celsius. The curve labeled 706 corresponds to the average temperature within the first sub-zone 706. The curve labeled 708 shows the temperature in the second sub-zone 708.

The dotted line 710 indicates the temperature of 41° C. which is the target temperature in this experiment. The dotted line 712 at one minute indicates the time once heating was started. The dotted line 714 which corresponds to 11 minutes indicates the time when heating stopped. It can be seen by examining chart 704 that the method is able to maintain the temperature of the target zone effectively.

FIG. 7 illustrates an experiment testing mild hyperthermia for a large volume heating algorithm: in vivo example. A treatment volume was selected inside a V×2 tumor in the thigh of a rabbit. A) Treatment volume location and its automatic partitioning into subvolumes, each of which can be treated with electronic steering alone. B) Temperature map immediately upon both sub-volumes having $T_{average}$>40° C., showing conformal heating of the entire treatment volume. C) Evolution of heating in both sub-volumes over the course of a 10-minute mild hyperthermia treatment.

Embodiments may incorporate one or more of these improvements or enhancements:

1) 3D MR thermometry imaging—The use of 3D MR thermometry in conjunction with the large volume heating approach described herein could enable better control over possible hot and/or cool-spots in real-time as well as provide more complete knowledge about tissue temperature distribution. Such information could improve the safety of this technique as well as provide higher quality of data for studies of drug delivery and radiation effects. Finally, use of 3D MR thermometry would allow for isotropic or near-isotropic voxel dimensions (3D imaging allows for thinner slices in MR thermometry), which could improve the accuracy of the treatment. Collection of focal spot offsets described above has been performed using 3D to increase spatial precision of the correction, and improvement in SNR through the use of different MR imaging coils can allow for 3D imaging to be used with sufficiently fast dynamic imaging for temperature monitoring during treatment.

2) Expansion to 3D treatment planning, execution, and monitoring—All of the example techniques and algorithms and embodiments are readily applicable to both 2D and 3D treatment planning Subdivision of a target volume into subvolumes can be accomplished in 3D using similar routines. Furthermore, the MR-HIFU platform allows for multi-dimensional mechanical movement of the transducer as well as multi-dimensional electronic steering, thus allowing for the entire treatment to take into account 3D geometry of the target as well as healthy tissues. Combination of 3D treatment planning with 3D imaging (see "Improvements or enhancements"/"3D MR thermometry imaging") could ensure that the treatment is directed with greatest possible specificity to its target.

3) Variable timing of the sonication and transducer movement—Each sonication may or may not be limited to the duration of one dynamic image acquisition. In the case where short dynamic image acquisition times are used, or in cases where fast heating/high power is required, sonication and/or movement commands may be issued or updated upon each image acquisition. However, if the imaging time is increased, as may be necessary to increase signal-to-noise ratio or acquire large volumes of data, both heating and movement to another location can be accomplished within one dynamic acquision.

4) Ability to use power and resultant heat to measure heat loss or perfusion—Real-time MR thermometry and application of ultrasound energy may allow for relative perfusion in heated tissue to be determined, based on evolution of temperature during heating of each of the subvolumes, while some subvolumes are cooling, as well as from the cooling following completion of hyperthermia. Finally, since the algorithm heats tissue only when needed and selects power based on temperature in each voxel (power calculation varies with feedback method), cumulative as well as instantaneous power required to maintain tissue at target temperature (as well as to heat up to that temperature) may be used to assess tissue perfusion. The pattern of perfusion in a tumor may provide insight into which parts of the tumor may best be treated with a combination of mild hyperthermia and chemotherapy or radiation, as well as to plan future treatments.

5) More robust automated focal spot deflection correction—The current implementation allows for both automatic and manual collection of focal spot deflection corrections at each transducer position. Tissue movement as well as local magnetic inhomogeneity or local areas of low SNR may result in erroneous detection of high temperature during the offset correction routine outlined in this application. Such errors could result in spatial inaccuracies of heating, which have so far been alleviated through addition of a manual adjustment. A more robust automatic detection algorithm that is better able to filter out possible errors in estimation of these correction factors could decrease the treatment planning time as well as ensure greater spatial precision of heating.

6) Real-time subvolume updates—The current implementation of the large volume algorithm subdivides the target volume into subvolumes immediately prior to beginning of hyperthermia treatment. However, this process is not computationally expensive (<0.2 s on a typical workstation), and therefore it can be performed in real time during heating or transducer movement. Such a real-time adjustment may be used to decrease the amount of mechanical movement of the transducer, cutting down on equipment maintenance costs and possibly improving stability of heating by reducing cooling that occurs during movement (where heating while moving is not possible, as in the case of several disconnected regions).

7) Smart, real-time calculation of optimal transducer movement—While the current implementation heats the coolest of the subvolumes when necessary, prioritization of movement may allow for further optimization, resulting in more efficient, possibly safer heating. Movement of the transducer causes artefacts in MR thermometry, which could affect temperature feedback and therefore must be either minimized or accounted for. Examples may account for the artefacts by ignoring those MR thermometry images that were acquired during transducer movement and through the use of multi-baseline imaging. The artifacts could also be minimized by minimizing the time and/or the distance that the transducer moves. This can be accomplished by moving the transducer along the shortest path. In order to heat peripheral parts of a target volume (the part that borders unheated tissue and therefore experiences the greatest relative heat loss), it may also be necessary to move the transducer along the longest path. Furthermore, the rate of tissue cooling and the rate of transducer movement can be used to select a subvolume that is optimally positioned to ensure minimal cooling during mechanical movement of the transducer towards it. This can be used in conjunction with real-time subvolume updates and with other embodiments outlined herein.

Use of multiple size electronic deflection limits—Subdivision of the target volume into subvolumes using a single electronic deflection limit is sufficient for large volume, conformal heating, as demonstrated by the data presented in this ID. However, the use of variable or multiple size electronic deflection limits may allow for more faster heating, especially if combined with real-time updates of volume partitioning outlined above. The use of smaller electronic deflection limits can allow for greater spatial precision of heating (focal spot is more diffuse with increased deflection) that could be useful in heating areas close to vital structures (next to blood vessels or nerves), whereas larger deflection limits can be used to heat subvolumes that do not require precise spatial definitions (such as tumor tissue away from tumor margins).

8) Ability to include margin around an intended region—the significant increase in maximum heated volume afforded by the large conformal volume MR-HIFU algorithm may allow for margins to be heated around a lesion (including larger lesions commonly seen in the clinic), possibly enhancing treatment efficacy.

9) Ability to plan and execute a combined ablation and mild hyperthermia treatment—the MR-HIFU system is capable of both ablation and mild hyperthermia heating. This advantage of the system could be used along with the other abovementioned features and improvements to ensure optimal treatment. Treatment planning can incorporate knowledge about tumor heterogeneity, such as the pattern of perfusion in the tumor, to ensure that different parts of the tumor are treated using approaches that could maximize efficacy of treatment. For example, areas that are poorly perfused may be best treated with ablation, whereas areas that are better perfused may be more amenable to a combination of hyperthermia and chemotherapy.

Applications for the large volume conformal mild hyperthermia algorithm include MR-guided pain palliation, MR-guided radiation sensitization, MR guided chemotherapeutic delivery (local drug delivery), MR guided drug activation, MR guided gene delivery and gene expression, and inducing physiological and cellular changes (under MR guidance) in order to provide clinical benefits. Many of the algorithms (volume partitioning) may be used for ablation (T>55° C.) treatments as well. One of the key advantages of using MR-HIFU for these purposes is its ability to provide image guidance and precise targeting of a lesion. Another possible advantage is the use of a variety of imaging data, such as contrast agent release from liposomes or tissue transport parameters for intraprocedural feedback. This could greatly expand the size of lesions or volumes that could be treated with the combination of mild hyperthermia and chemotherapy or radiotherapy.

Figure 8:
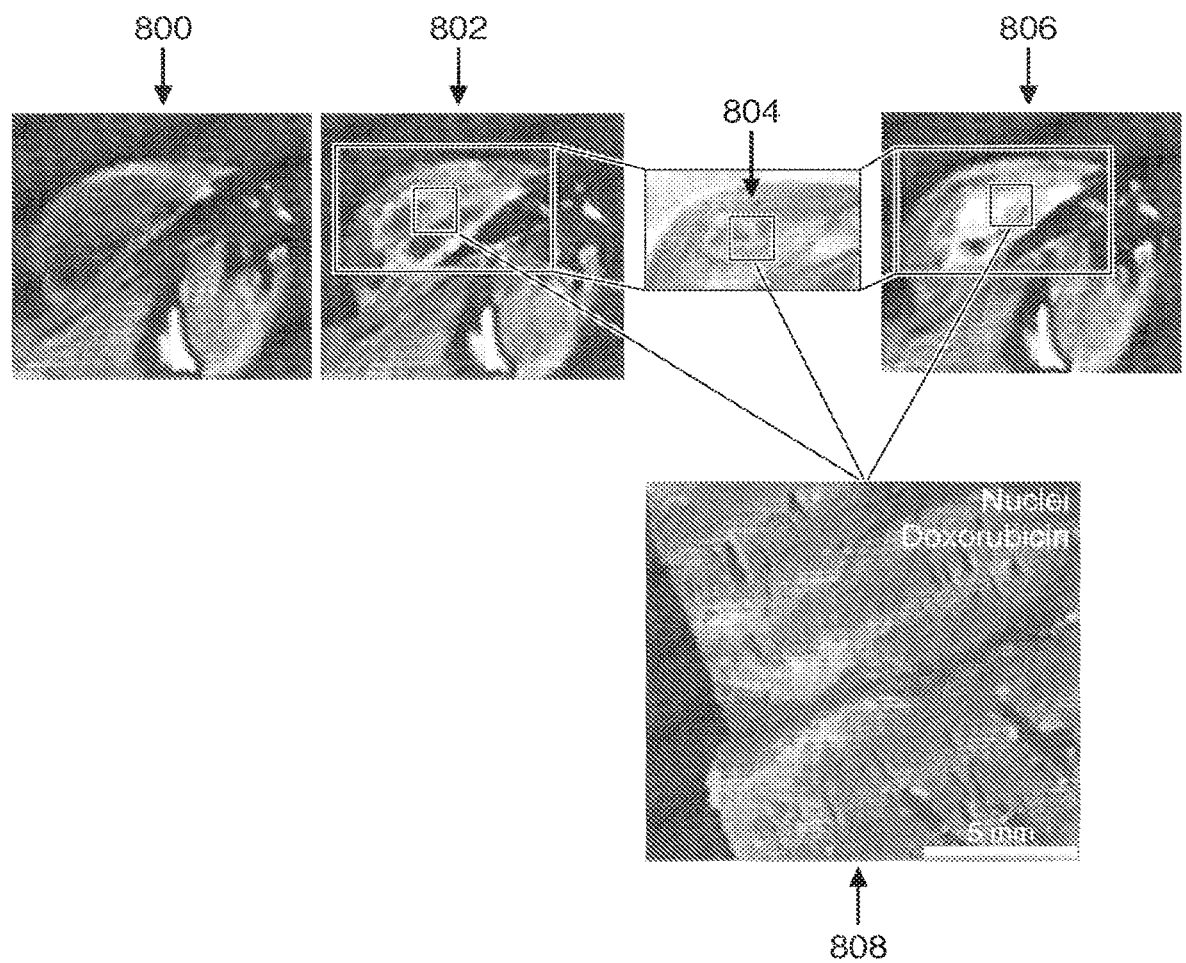
FIG. 8 illustrates magnetic resonance signal intensity and doxorubicin fluorescence after imageable low temperature sensitive liposome (iLTSL) injection and heating with magnetic resonance high-intensity focused ultrasound.

FIG. 8 illustrates magnetic resonance signal intensity and doxorubicin fluorescence after iLTSL injection and heating with magnetic resonance high-intensity focused ultrasound. Image 800 shows the signal intensity before the iLTSL injection. Image 802 shows the signal intensity after iLTSL injection. Image 804 shows an example of a temperature map during heating overlaid on a signal intensity obtained with the treatment planning proton density weighted scan. FIG. 806 shows the signal intensity after four ten minute heating sessions. FIG. 808 shows the doxorubicin fluorescence in the approximate location of heating.

As mentioned above, FIG. 9 illustrates MR signal intensity and doxorubicin fluorescence after iLTSL injection and heating with MR-HIFU. Signal intensity image 800) before iLTSL injection and image 802) after iLTSL injection. Image 804) Example of temperature map during heating, overlaid on signal intensity obtained with a treatment planning proton density weighted scan. Image 806) Signal intensity after four 10-minute heating sessions. Image 808) Doxorubicin fluorescence in the approximate location of heating. Note that images 800, 802, and 806 depict T1-weighted images whereas image 804 shows a proton density weighted image.

In some instances it may be useful to perform a multi-baseline correction. The motion of the ultrasonic transducer may interfere with the magnetic resonance imaging. This may cause artifacts in phase images and obstruct temperature changes. This may be removed by performing multi-baseline imaging. This is performed by collecting magnetic resonance phase images in every single transducer location before heating has started and then may subtract the appropriate images from the phase images collected during heating. In some instances it may also be useful to correct the natural focus offset. In tissue identity or geometry may cause real focuses to deviate from a natural focus. This may necessitate a transducer location specific correction. It may be useful to calculate a natural focus offset for every transducer location. This may be implemented plane by plane. In some instances it may be useful to correct the power and compensate for out of plane heating. When greater electronic deflection is used it causes defocusing which causes a reduction in power. This may also increase the near field heating by the ultrasound transducer. For the near field heating it may be useful to add a spatial offset to correct the position of the transducer. For the reduction in power caused by defocusing it may be useful to increase the power output to compensate for this decrease in power.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

REFERENCES

[1] M. O. Kohler, C. Mougenot, B. Quesson et al., "Volumetric HIFU ablation under 3D guidance of rapid MRI thermometry," Med Phys, vol. 36, no. 8, pp. 3521-35, August, 2009.
[2] R. Staruch, R. Chopra, and K. Hynynen, "Localised drug release using MRI-controlled focused ultrasound hyperthermia," Int J Hyperthermia, vol. 27, no. 2, pp. 156-71, 2011.
[3] P. M. Harari, K. H. Hynynen, R. B. Roemer et al., "Development of scanned focussed ultrasound hyperthermia: clinical response evaluation," Int J Radiat Oncol Biol Phys, vol. 21, no. 3, pp. 831-40, August, 1991.
[4] J. K. Enholm, M. O. Kohler, B. Quesson et al., "Improved volumetric MR-HIFU ablation by robust binary feedback control," IEEE Trans Biomed Eng, vol. 57, no. 1, pp. 103-13, January, 2010.

LIST OF REFERENCE NUMERALS 200 medical instrument
202 magnetic resonance imaging system
204 high-intensity focused ultrasound system
206 magnet
208 bore of magnet
210 magnetic field gradient coil
212 magnetic field gradient coil power supply
214 radio frequency coil
216 transceiver
218 imaging zone
220 subject
222 subject support
224 fluid filled chamber
226 ultrasonic transducer
228 mechanical positioning system
230 actuator
232 path of ultrasound
234 ultrasound window
236 gel pad
238 focus
240 target zone
242 computer system
244 processor
246 hardware interface 248 user interface
250 computer storage
252 computer memory
260 focusing zone definition
262 target zone coordinates
264 sub-zone coordinates
266 transducer position coordinates
268 pulse sequence
270 magnetic resonance thermometry data
272 sequence
274 temperature property map
280 control module
282 sub-zone division module
284 image reconstruction module
286 temperature control algorithm
288 sub-zone selection algorithm
300 imaging
302 magnetic resonance thermometry
304 treatment planning
306 sonication—feedback cycle
308 treatment zone partitioning algorithm
310 multi-baseline correction
312 transducer spatial offset correction
314 temperature feedback control
316 decision tree
318 mechanical movement
400 view of target zone
402 view of target zone
404 view of target zone
406 medial axis
408 center of mass
410 furthers voxel
412 focal point
414 focusing zone
416 sub-zone 1
418 sub-zone 2
420 sub-zone 3
422 sub-zone 4
424 sub-zone 5
426 sub-zone 6
428 sub-zone 7
430 sub-zone 8
500 acquisition of magnetic resonance thermometry data
502 decision tree
504 result of decision
506 next sub-zone to be heated
600 decision
602 imaging
604 delay
606 heating
608 moving
610 time (s)
700 planning image
702 thermal image
704 chart time vs. temperature
706 first sub-zone
708 second sub-zone
710 average temperature
712 heating started
714 heating stopped

The invention claimed is:

1. A medical instrument comprising:
a magnetic resonance imaging system that acquires magnetic resonance thermometry data from a subject within an imaging zone;
a high-intensity focused ultrasound system comprising:
an ultrasound transducer with an electronically-controlled focus, the electronically-controlled focus being adjustable within a focusing zone; and
a mechanical positioning system that positions the ultrasound transducer to set a location of the focusing zone;
a memory for storing machine executable instructions;
a processor for controlling the medical instrument, wherein execution of the instructions causes the processor to:
receive a target zone descriptive of a volume within the subject,
wherein the target zone is larger than the focusing zone;
divide the target zone into multiple sub-zones, wherein each of the multiple sub-zones has a corresponding transducer position, and when the ultrasound transducer is at the corresponding transducer position: (1) the sub-zone is fully disposed within the focusing zone and (2) the sub-zone can be treated using the electronically-controlled focus alone;
determine a sequence for moving the transducer position to each of the multiple sub-zones into which the target zone was divided;
determine a selected sub-zone selected from the multiple sub-zones using the sequence, wherein each of the sub-zones is divided into regions;
wherein execution of the instructions further cause the processor to maintain the target zone at a target temperature for a predetermined time duration by repeatedly:
controlling the mechanical positioning system to move the ultrasound transducer to the corresponding transducer position of the selected sub-zone;
acquiring the magnetic resonance thermometry data, wherein the magnetic resonance thermometry data is descriptive of a temperature of voxels in the sub-zone;
determining a temperature property map descriptive of the temperature in each of the voxels using at least the magnetic resonance thermometry data;
heating the regions of the sub-zone independently to the target temperature by controlling the electronically-controlled focus with a temperature feedback algorithm that uses the temperature property map; and
changing the selected sub-zone using the sequence;
wherein execution of the instructions further causes the processor to:
after start of said heating, determine a temperature property: (i) for each of the multiple sub-zones into which the target zone was divided (ii) using the magnetic resonance thermometry data;
after said determine a temperature property after said start of said heating, select a next sub-zone: (i) from the multiple sub-zones into which the target zone was divided (ii) using the temperature property for each of the multiple sub-zones into which the target zone was divided; and
after said select a next sub-zone from the multiple sub-zones after said determine a temperature property after said start of said heating, modify the sequence for moving the transducer position to each of the multiple sub-zones into which the target zone was divided such that said next sub-zone: (i) which was selected from the multiple sub-zones into which the target zone was divided (ii) is sequentially next in the sequence; and wherein execution of the instructions further causes the processor to repeatedly calculate perfusion coefficients and/or diffusion coefficients for each of the voxels using magnetic resonance data.

2. The medical instrument of claim 1, wherein execution of the instructions further causes the processor to control the mechanical positioning system to move the ultrasound transducer to the corresponding transducer position for each of the multiple sub-zones before heating the target zone to the target temperature.

3. The medical instrument of claim 2, wherein execution of the instructions further causes the processor to acquire calibration magnetic resonance thermometry data while at the corresponding transducer position for each of the multiple sub-zones before heating the target zone to the target temperature, and wherein the temperature property map is determined using at least the calibration magnetic resonance data.

4. The medical instrument of claim 2, wherein execution of the instructions further causes the processor to:
perform a test ultrasound exposure using the high-intensity focused ultrasound system while at the corresponding transducer position for each of two or more of the multiple sub-zones before heating the target zone to the target temperature; and
determine an electronic focus correction for each of the multiple sub-zones and/or adjust the location of the focusing zone for each of the two or more of the multiple sub-zones and/or calculate a temperature rise rate for each of the multiple sub-zones.

5. The medical instrument of claim 1, wherein the temperature feedback control algorithm has temperature control algorithm parameters, wherein execution of the instructions further causes the processor to repeatedly recalculate the temperature control algorithm parameters using the perfusion coefficients and/or diffusion coefficients.

6. The medical instrument of claim 1, wherein the temperature feedback control algorithm is any one of the following: a binary temperature control algorithm, a proportional temperature control algorithm, a proportional-integral temperature control algorithm, or a proportional-integral-derivative temperature control algorithm.

7. The medical instrument of claim 1, wherein the target zone is divided into the multiple sub-zones using a medial axial transformation.

8. The medical instrument of claim 1, wherein the medical instrument comprises a fluid cooling system that circulates a fluid for cooling the subject, wherein the fluid cooling system is operable for maintaining the fluid at an operating temperature, wherein execution of the instructions further causes the processor to:
repeatedly acquire magnetic resonance data descriptive of the spin phase of the fluid to determine a change in the spin phase; and
correct the temperature property map using the change in the spin phase of the fluid.

9. The medical instrument of claim 1, wherein execution of the instructions further causes the processor to adjust the size and/or location of the sub- zones and or the transducer position after starting to maintain the target zone at target temperature.

10. The medical instrument of claim 1, wherein heating the regions of the sub-zone comprises generating ultrasound using the ultrasound transducer and execution of the instructions further causes the processor to generate the ultrasound while changing the selected sub-zone.

11. The medical instrument of claim 1, wherein a decision tree algorithm is used to initiate changing the selected sub-zone.

12. The medical instrument of claim 1, wherein the target temperature is any one of the following: between 38° C. and 40° C., between 39° C. and 40° C., between 40 and 45 degrees Celsius, between 40 and 44 degrees Celsius, between 40 and 43 degrees Celsius, between 40 and 42 degrees Celsius, between 40 and 41 degrees Celsius, between 41 and 45 degrees Celsius, between 41 and 44 degrees Celsius, between 41 and 43 degrees Celsius, between 41 and 42 degrees Celsius, between 42 and 45 degrees Celsius, between 42 and 44 degrees Celsius, between 42 and 43 degrees Celsius, between 43 and 45 degrees Celsius, between 43 and 44 degrees Celsius, between 44 and 45 degrees Celsius, between 38 and 39 degrees Celsius, between 52 and 55 degrees Celsius, greater than or equal to 55 degrees Celsius, and between 50 and 55 degrees Celsius.

13. The medical instrument of claim 1, wherein the sequence for moving the transducer position to each of the multiple sub-zones is based on an average temperature of each sub-zone.

14. The medical instrument of claim 13, wherein the selected sub-zone has a lowest average temperature of each sub-zone.

15. A computer program product comprising a computer-readable non-transitory storage medium that stores machine executable instructions for execution by a processor controlling a medical instrument wherein execution of the instructions causes the processor to:
receive a target zone descriptive of a volume within a subject, wherein the target zone is larger than a focusing zone of an ultrasound transducer in a high-intensity focused ultrasound system, the ultrasound transducer having an electronically-controlled focus that is adjustable within the focusing zone;
divide the target zone into multiple sub-zones, wherein each of the multiple sub-zones has a corresponding transducer position, and when the ultrasound transducer is at the corresponding transducer position: (1) the sub-zone is fully disposed within the focusing zone and (2) the sub-zone can be treated using the electronically-controlled focus alone, wherein each sub-zone is divided into regions;
determine a sequence for moving the transducer position to each of the multiple sub-zones into which the target zone was divided;
determine a selected sub-zone selected from the multiple sub-zones using the sequence;
wherein execution of the instructions further cause the processor to maintain the target zone at a target temperature for a predetermined time duration by repeatedly:
controlling a mechanical positioning system to move the ultrasound transducer to the corresponding transducer position of the selected sub-zone;
acquiring magnetic resonance thermometry data from the subject within an imaging zone using a magnetic resonance imaging system, wherein the magnetic resonance thermometry data is descriptive of a temperature of voxels in the sub-zone;
determining a temperature property map descriptive of the temperature in each of the voxels using at least the magnetic resonance thermometry data;
heating each region independently to the target temperature by controlling the electronically-controlled focus with a temperature feedback algorithm that uses the temperature property map; and changing the selected sub-zone using the sequence;

wherein execution of the instructions further causes the processor to:

after start of said heating, determine a temperature property: (i) for each of the multiple sub-zones into which the target zone was divided (ii) using the magnetic resonance thermometry data;

after said determine a temperature property after said start of said heating, select a next sub-zone: (i) from the multiple sub-zones into which the target zone was divided (ii) using the temperature property for each of the multiple sub-zones into which the target zone was divided; and after said select a next sub-zone from the multiple sub-zones after said determine a temperature property after said start of said heating, modify the sequence for moving the transducer position to each of the multiple sub-zones into which the target zone was divided such that said next sub-zone: (i) which was selected from the multiple sub-zones into which the target zone was divided (ii) is sequentially next in the sequence; and wherein execution of the instructions further causes the processor to repeatedly calculate perfusion coefficients and/or diffusion coefficients for each of the voxels using magnetic resonance data.

16. The computer program product of claim 15, wherein the sequence for moving the transducer position to each of the multiple sub-zones is based on an average temperature of each sub-zone.

17. The computer program product of claim 16, wherein the selected sub-zone has a lowest average temperature of each sub-zone.

* * * * *